US009994887B2

(12) United States Patent
Gong et al.

(10) Patent No.: US 9,994,887 B2
(45) Date of Patent: *Jun. 12, 2018

(54) METHODS AND COMPOSITIONS FOR IMPROVING EFFICIENCY OF NUCLEIC ACIDS AMPLIFICATION REACTIONS

(71) Applicant: Bio-Rad Laboratories, Inc., Hercules, CA (US)

(72) Inventors: Xiao-Song Gong, Berkeley, CA (US); John Sullivan, Oakland, CA (US); Rongdian Fu, El Cerrito, CA (US); Yan Wang, San Francisco, CA (US); Evan H. Bursey, Concord, CA (US); Man Cheng, San Ramon, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/482,756

(22) Filed: Sep. 10, 2014

(65) Prior Publication Data

US 2014/0377767 A1 Dec. 25, 2014

Related U.S. Application Data

(63) Continuation of application No. 12/683,950, filed on Jan. 7, 2010, now Pat. No. 8,859,205.

(60) Provisional application No. 61/143,350, filed on Jan. 8, 2009.

(51) Int. Cl.
*C12Q 1/68* (2018.01)
*C12P 19/34* (2006.01)
*C07K 16/40* (2006.01)
*C12N 9/12* (2006.01)

(52) U.S. Cl.
CPC .............. *C12P 19/34* (2013.01); *C07K 16/40* (2013.01); *C12N 9/1252* (2013.01); *C12Q 1/6804* (2013.01); *C12Q 1/686* (2013.01); *C07K 2317/56* (2013.01); *C07K 2317/565* (2013.01); *C07K 2317/76* (2013.01); *C07K 2319/80* (2013.01)

(58) Field of Classification Search
None
See application file for complete search history.

(56) References Cited

U.S. PATENT DOCUMENTS

| | | | |
|---|---|---|---|
| 5,489,523 A | 2/1996 | Mathur et al. | |
| 6,025,545 A | 2/2000 | Lundquist et al. | |
| 6,174,670 B1 * | 1/2001 | Wittwer et al. | 435/6.12 |
| 6,673,578 B1 * | 1/2004 | Uemori et al. | 435/91.2 |
| 8,859,205 B2 * | 10/2014 | Gong et al. | 435/6.12 |
| 2004/0081963 A1 * | 4/2004 | Wang | C12N 9/1252 435/6.11 |
| 2004/0219558 A1 * | 11/2004 | Vander Horn et al. | 435/6 |
| 2005/0069908 A1 | 3/2005 | Sorge et al. | |
| 2006/0172324 A1 | 8/2006 | Wang et al. | |
| 2007/0141591 A1 * | 6/2007 | Borns | 435/6 |
| 2009/0286251 A1 | 11/2009 | Xu | |

FOREIGN PATENT DOCUMENTS

| | | |
|---|---|---|
| EP | 0 821 058 B1 | 11/2006 |
| WO | 2004/011605 A2 | 2/2004 |
| WO | 2004087868 A2 | 10/2004 |
| WO | 2005/059159 A2 | 6/2005 |
| WO | 2007/011891 A2 | 1/2007 |

OTHER PUBLICATIONS

Hernandez et al., "Development of real-time PCR systems based on SYBR® Green I, Amplifluor™ and TaqMan® technologies for specific quantitative detection of the transgenic maize even GA21," Journal of Cereal Science, 2004, vol. 39, pp. 99-107.*
International Preliminary Report on Patentability dated Jul. 12, 2011 from International Patent Application No. PCT/US2010/020371, 7 pages.
Supplemental European Search Report from EP 10729512.3 dated Nov. 15, 2012.
Arezi et al.; "Amplification efficiency of thermostable DNA polymerases"; *Analytical Biochemistry*; 321:226-235 (2003).
Haqqi et al., "Sequencing in the Presence of Betaine: Improvement in Sequencing of the Localized Repeat Sequence Regions"; *Journal of Biomolecular Techniques*; 13(4):265-271 (2002).
Henke, Wolfgang et al.; "Betaine improves the PCR amplification of GC-rich DNA sequences"; 1997, *Nucleic Acids Research*, vol. 25, No. 19, pp. 3957-3958.
Holodniy et al.; "Inhibition of Human Immunodeficiency Virus Gene Amplification by Heparin"; *J. Clin. Microbiol.*; 29(4):676-679 (1991).
Liu et al.; "The Peptide Backbone Plays a Dominant Role in Protein Stabilization by Naturally Occurring Osmolytes"; *Biochemistry*; 34:12884-12891 (1995).
Mytelka et al.; "Analysis and suppression of DNA polymerase pauses associated with a trinucleotide consensus"; *Nucl. Acids Res.*; 24(14):2774-2781 (1996).
Rajendrakumar et al.; "DNA helix destabilization by proline and betaine: possible role in the salinity tolerance process"; *FEBS Letters*; 410(2-3):201-205 (Jun. 1997).
Rees et al.; "Betaine can eliminate the base pair composition dependence of DNA melting"; *Biochemistry*; 32:137-144 (1993).
Santoro et al.; "Increased thermal stability of proteins in the presence of naturally occurring osmolytes"; 31:5278-5283 (1992).
Thakar et al.; "Osmolyte Mediation of T7 DNA polymerase and Plasmid DNA Stability"; *Biochemistry*; 33:12255-12259 (1994).

(Continued)

*Primary Examiner* — Young J Kim
(74) *Attorney, Agent, or Firm* — Kilpatrick Townsend and Stockton LLP

(57) ABSTRACT

The present invention provides methods and compositions for improving the efficiency of nucleic acid amplification reactions. The invention encompasses hybrid polymerases that show increased processivity over wild type polymerases as well as decreased exonucleases activity. The invention also encompasses methods, compositions and kits for conducting nucleic acid synthesis and amplification reactions in which non-specific amplification of primers is reduced.

7 Claims, 5 Drawing Sheets

(56) References Cited

OTHER PUBLICATIONS

Weissensteiner et al.; "Strategy for Controlling Preferential Amplification and Avoiding False Negatives in PCR Typing"; BioTechniques; 21:1102-1108 (Dec. 1996).
The extended European Search Report from EP 15155113.2 dated May 27, 2015.
Li, et al., "Universal molecular beacon-based tracer system for real-time polymerase chain reaction", *Anal. Chem.*, vol. 78, pp. 7886-7890 (2006).
EP Patent Application No. 15155113.2 "Communication pursuant to Article 94(3) EPC", dated Dec. 14, 2016, 5 pages.
Hopfner, K-P. et al.; "Crystal structure of a thermostable type B DNA polymerase from *Thermococcus gorgonarius*"; Proc. Natl. Acad. Sci. USA; Mar. 1999; pp. 3600-3605; vol. 96.
Hashimoto, H. et al.; "Crystal Structure of DNA Polymerase from Hyperthermophilic Archaeon Pyrococcus kodakaraensis KOD1"; J. Mol. Biol.; 2001; pp. 469-477; vol. 306.
Maxim Biomedical, Inc.; "Quantitative Competitive PCR Kit for Human CD40; Cat No. ZP-10007; Instruction Manual"; Sep. 18, 2002; 12 pages; South San Francisco, California, US.
Takara Biomedicals, "Competitive PCR Guide; Lit. #L0126"; Aug. 1999; 9 pages, Kusatsu, Shiga, Japan.

\* cited by examiner

MILDADYITEEGKPVIRLFKKENGEFKIEHDRTFRPYIYALLKDDSKIEEVKKITAERHGKI
VRIVDAEKVEKKFLGRPITVWRLYFEHPQDVPTIREKIREHSAVVDIFEYDIPFAKRYLID
KGLIPMEGDEELKLLAFAIATLYHEGEEFGKGPIIMISYADEEEAKVITWKKIDLPYVEVV
SSEREMIKRFLKIIREKDPDIIITYNGDSFDLPYLAKRAEKLGIKLTIGRDGSEPKMQRIGD
MTAVEVKGRIHFDLYHVIRRTINLPTYTLEAVYEAIFGKPKEKVYADEIAKAWETGEGL
ERVAKYSMEDAKATYELGKEFFPMEAQLSRLVGQPLWDVSRSSTGNLVEWFLLRKAY
ERNELAPNKPDEREYERRLRESYAGGFVKEPEKGLWENIVSLDFRALYPSIIITHNVSPDT
LNREGCRNYDVAPEVGHKFCKDFPGFIPSLLKRLLDERQKIKTKMKASQDPIEKIMLDY
RQRAIKILANSYYGYYGYAKARWYCKECAESVTAWGREYIEFVWKELEEKFGFKVLYI
DTDGLYATIPGGKSEEIKKKALEFVDYINAKLPGLLELEYEGFYKRGFFVTKKKYALIDE
EGKIITRGLEIVRRDWSEIAKETQARVLEAILKHGNVEEAVRIVKEVTQKLSKYEIPPEKL
AIYEQITRPLHEYKAIGPHVAVAKRLAAKGVKIKPGMVIGYIVLRGDGPISNRAILAEEY
DPRKHKYDAEYYIENQVLPAVLRILEGFGYRKEDLRWQKTKQTGLTSWLNIKKSGTGG
GGATVKFKYKGEEKEVDISKIKKVWRVGKMISFTYDEGGGKTGRGAVSEKDAPKELLQ
MLEKQKK*

FIG. 4A

ATVKFKYKGEEKEVDISKIKKVWRVGKMISFTYDEGGGKTGRGAVSEKDAPKELLQML
EKQKK

SEQUENCE LISTING

<160> NUMBER OF SEQ ID NOS: 47

<210> SEQ ID NO 1
<211> LENGTH: 2535
<212> TYPE: DNA
<213> ORGANISM: Artificial Sequence
<220> FEATURE:
<223> OTHER INFORMATION: synthetic hybrid polymerase with polymerase
      domain and heterologous DNA binding domain

<400> SEQUENCE: 1

```
atgatcctgg atgctgacta catcactgaa gaaggcaaac cggttatccg tctgttcaaa      60
aaagagaacg gcgaatttaa gattgagcat gatcgcacct ttcgtccata catttacgct     120
ctgctgaaag atgattctaa gattgaggaa gttaaaaaaa tcactgctga gcgccatggc     180
aagattgttc gtatcgttga tgcggaaaag gtagaaaaga aatttctggg cagaccaatc     240
accgtgtgga gactgtattt cgaacatcca caagatgttc gactattcg cgagaaaatt     300 cgcgaacatt ctgcagttgt tgacatcttc gaatacgata ttccatttgc aaagcgttac     360
ctcatcgaca aaggcctgat accaatggag ggcgatgaag aactcaagct cctggcgttc     420
gctatagcaa ccctctatca cgaaggcgaa gagtttggta aaggcccaat tataatgatc     480
agctatgcag atgaagaaga agcaaaggtg attacttgga aaaaaataga tctcccatac     540
gttgaggttg tatcttccga gcgcgagatg attaagcgct ttctcaaaat tatccgcgag     600
aaggatccgg acattatcat tacttataac ggcgactctt ttgacctccc atatctggcg     660
aaacgcgcag aaaaactcgg tattaaactg actatcggcc gtgatggttc cgagccgaag     720
atgcagcgta tcggcgatat gaccgctgta gaagttaagg gtcgtatcca tttcgacctg     780
tatcatgtaa ttcgtcgtac tattaacctc ccgacttaca ctctcgaggc tgtatatgaa     840 gcaattttg gtaagccgaa ggagaaggta tacgccgatg agattgcaaa ggcgtgggaa     900
accggtgagg gcctcgagcg tgttgcaaaa tactccatgg aagatgcaaa ggcgacttat     960
gaactcggca agaattctt cccaatggaa gctcagctct ctcgcctggt tggccaacca    1020
ctgtgggatg tttctcgttc ttccaccggt aacctcgtag agtggttct cctgcgcaaa    1080 gcgtacgaac gcaacgaact ggctccgaac aagccagatg aacgtgagta tgaacgccgt    1140
ctccgcgagt cttacgctgg tggctttgtt aaagagccag aaagggcct ctgggaaaac    1200 atcgtgtccc tcgattttcg cgctctgtat ccgtctatta tcattaccca caacgtgtct    1260
ccggatactc tcaaccgcga gggctgcaga aactatgatg ttgctccgga agtaggccac    1320
aagttctgca aggacttccc gggctttatt ccgtctctcc tgaaacgtct gctcgatgaa    1380
cgccaaaaga ttaagactaa aatgaaggcg tcccaggatc gattgaaaa ataatgctc    1440 gactatcgcc aaagagcgat taaatcctc gcaaactctt attacggcta ttatggctat    1500
gcaaaagcac gctggtactg taaggagtgt gctgagtccg ttactgcttg ggtcgcgaa    1560 tacatcgagt tcgtgtggaa ggagctcgaa gaaaagtttg gctttaaagt tctctacatt    1620
gacactgatg gtctctatgc gactattccg ggtggtaagt ctgaggaaat taagaaaag    1680
```

-continued

```
gctctagaat tgtggatta cattaacgcg aagctcccgg gtctcctgga gctcgaatat    1740
gaaggctttt ataaacgcgg cttcttcgtt accaagaaga aatatgcgct gattgatgaa    1800
gaaggcaaaa ttattactcg tggtctcgag attgtgcgcc gtgattggag cgaaattgcg    1860
aaagaaactc aagctagagt tctcgaggct attctcaaac acggcaacgt tgaagaagct    1920
gtgagaattg taaagaagt aacccaaaag ctctctaaat atgaaattcc gccagagaag    1980
ctcgcgattt atgagcagat tactcgcccg ctgcatgagt ataaggcgat tggtccgcac    2040
gtggctgttg caaagagact ggctgctaaa ggcgtgaaaa ttaaaccggg tatggtaatt    2100
ggctacattg tactccgcgg cgatggtccg attagcaacc gtgcaattct agctgaggaa    2160
tacgatccga aaagcacaa gtatgacgca gaatattaca ttgagaacca ggtgctcccg    2220
gcggtactcc gtattctgga gggttttggc taccgtaagg aagacctccg ctggcaaaag    2280
actaaacaga ctggcctcac ttcttggctc aacattaaaa aatccggtac cggcggtggc    2340
ggtgcaaccg taaagttcaa gtacaaaggc gaagaaaaag aggtagacat ctccaagatc    2400
aagaaagtat ggcgtgtggg caagatgatc tccttcacct acgacgaggg cggtggcaag    2460
accggccgtg gtgcggtaag cgaaaaggac gcgccgaagg agctgctgca gatgctggag    2520
aagcagaaaa agtga                                                     2535
```

<210> SEQ ID NO 2
<211> LENGTH: 844
<212> TYPE: PRT
<213> ORGANISM: Artificial Sequence
<220> FEATURE:
<223> OTHER INFORMATION: synthetic mutant hybrid polymerase with
      polymerase domain and heterologous DNA binding domain and two
      point mutations E141A and D143A to abolish 3'-5'
      exonuclease activity

<400> SEQUENCE: 2

```
Met Ile Leu Asp Ala Asp Tyr Ile Thr Glu Glu Gly Lys Pro Val Ile
  1               5                  10                  15
Arg Leu Phe Lys Lys Glu Asn Gly Glu Phe Lys Ile Glu His Asp Arg
             20                  25                  30
Thr Phe Arg Pro Tyr Ile Tyr Ala Leu Leu Lys Asp Asp Ser Lys Ile
         35                  40                  45
Glu Glu Val Lys Lys Ile Thr Ala Glu Arg His Gly Lys Ile Val Arg
     50                  55                  60
Ile Val Asp Ala Glu Lys Val Glu Lys Lys Phe Leu Gly Arg Pro Ile
 65                  70                  75                  80
Thr Val Trp Arg Leu Tyr Phe Glu His Pro Gln Asp Val Pro Thr Ile
                 85                  90                  95
Arg Glu Lys Ile Arg Glu His Ser Ala Val Val Asp Ile Phe Glu Tyr
            100                 105                 110
Asp Ile Pro Phe Ala Lys Arg Tyr Leu Ile Asp Lys Gly Leu Ile Pro
        115                 120                 125
Met Glu Gly Asp Glu Glu Leu Lys Leu Leu Ala Phe Ala Ile Ala Thr
    130                 135                 140
Leu Tyr His Glu Gly Glu Glu Phe Gly Lys Gly Pro Ile Ile Met Ile
145                 150                 155                 160
Ser Tyr Ala Asp Glu Glu Glu Ala Lys Val Ile Thr Trp Lys Lys Ile
                165                 170                 175
Asp Leu Pro Tyr Val Glu Val Val Ser Ser Glu Arg Glu Met Ile Lys
            180                 185                 190
```

-continued

Arg Phe Leu Lys Ile Ile Arg Glu Lys Asp Pro Asp Ile Ile Thr
            195                 200             205

Tyr Asn Gly Asp Ser Phe Asp Leu Pro Tyr Leu Ala Lys Arg Ala Glu
        210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Thr Gly Glu Gly
        290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
        370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ala Leu Tyr Pro Ser Ile Ile Ile Thr
                405                 410                 415

His Asn Val Ser Pro Asp Thr Leu Asn Arg Glu Gly Cys Arg Asn Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Lys Ile
450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
        515                 520                 525

Leu Glu Glu Lys Phe Gly Phe Lys Val Leu Tyr Ile Asp Thr Asp Gly
        530                 535                 540

Leu Tyr Ala Thr Ile Pro Gly Gly Lys Ser Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln

```
                  610                 615                 620

Ala Arg Val Leu Glu Ala Ile Leu Lys His Gly Asn Val Glu Ala
625                 630                 635                 640

Val Arg Ile Val Lys Glu Val Thr Gln Lys Leu Ser Lys Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Arg Leu Ala
            675                 680                 685

Ala Lys Gly Val Lys Ile Lys Pro Gly Met Val Ile Gly Tyr Ile Val
            690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
                740                 745                 750

Lys Glu Asp Leu Arg Trp Gln Lys Thr Lys Gln Thr Gly Leu Thr Ser
            755                 760                 765

Trp Leu Asn Ile Lys Lys Ser Gly Thr Gly Gly Gly Ala Thr Val
770                 775                 780

Lys Phe Lys Tyr Lys Gly Glu Glu Lys Glu Val Asp Ile Ser Lys Ile
785                 790                 795                 800

Lys Lys Val Trp Arg Val Gly Lys Met Ile Ser Phe Thr Tyr Asp Glu
                805                 810                 815

Gly Gly Gly Lys Thr Gly Arg Gly Ala Val Ser Glu Lys Asp Ala Pro
            820                 825                 830

Lys Glu Leu Leu Gln Met Leu Glu Lys Gln Lys Lys
            835                 840

<210> SEQ ID NO 3
<211> LENGTH: 63
<212> TYPE: PRT
<213> ORGANISM: Artificial Sequence
<220> FEATURE:
<223> OTHER INFORMATION: synthetic hyperthermophilic archaebacteria
      Sulfolobus solfataricus Sso7d heterologous DNA
      binding domain

<400> SEQUENCE: 3

Ala Thr Val Lys Phe Lys Tyr Lys Gly Glu Glu Lys Glu Val Asp Ile
1               5                   10                  15

Ser Lys Ile Lys Lys Val Trp Arg Val Gly Lys Met Ile Ser Phe Thr
            20                  25                  30

Tyr Asp Glu Gly Gly Gly Lys Thr Gly Arg Gly Ala Val Ser Glu Lys
        35                  40                  45

Asp Ala Pro Lys Glu Leu Leu Gln Met Leu Glu Lys Gln Lys Lys
    50                  55                  60

<210> SEQ ID NO 4
<211> LENGTH: 189
<212> TYPE: DNA
<213> ORGANISM: Artificial Sequence
<220> FEATURE:
<223> OTHER INFORMATION: synthetic nucleotide encoding mutant hybrid
      polymerase with polymerase domain and heterologous
      DNA binding domain and two point mutations E141A
      and D143A to abolish 3'-5' exonuclease activity
```

<400> SEQUENCE: 4

```
gcaaccgtaa agttcaagta caaaggcgaa gaaaaagagg tagacatctc caagatcaag    60
aaagtatggc gtgtgggcaa gatgatctcc ttcacctacg acgagggcgg tggcaagacc   120
ggccgtggtg cggtaagcga aaaggacgcg ccgaaggagc tgctgcagat gctggagaag   180
cagaaaaag                                                           189
```

<210> SEQ ID NO 5
<211> LENGTH: 6
<212> TYPE: PRT
<213> ORGANISM: Artificial Sequence
<220> FEATURE:
<223> OTHER INFORMATION: synthetic fusion protein peptide linker sequence

<400> SEQUENCE: 5

Gly Thr Gly Gly Gly Gly
 1               5

<210> SEQ ID NO 6
<211> LENGTH: 397
<212> TYPE: DNA
<213> ORGANISM: Artificial Sequence
<220> FEATURE:
<223> OTHER INFORMATION: synthetic monoclonal antibody M13-vh heavy-chain variable region

<400> SEQUENCE: 6

```
gaagtacagc tggagcagtc aggggctgag ctggtgaggc ctgggtcctc agtgaagatt    60
tcctgcaagg cttctggcta tgttttcagt acctactgga tgaactgggt gaagcagagg   120
cctggacagg gtcttgagtg gattggacag atttatcctg agatggtgg tgttaactac   180
aatggagagt tcaaggctag gccacactg actgcagaca gatcctccag cacagcctac   240
atgcagctca ggagcctaac atctgaggac tctgcggtct atttctgtgc aagttcttct   300
tactacggtg gtagttccgt ctcctggctt gcttactggg gccaagggac tctggtctct   360
gtctctgcag ccaaaacgac accccccatct gtctata                            397
```

<210> SEQ ID NO 7
<211> LENGTH: 391
<212> TYPE: DNA
<213> ORGANISM: Artificial Sequence
<220> FEATURE:
<223> OTHER INFORMATION: synthetic monoclonal antibody M15-vh heavy-chain variable region

<400> SEQUENCE: 7

```
gaagtaaagc tggaggagtc aggggctgag ttggcaagac ctggggcttc agtgaagttg    60
tcctgcaagg cttctggcta cacctttact agctactgga tgcagtgggt aaaacagagg   120
cctggacagg gtctggaatg gattggggct atttatcctg agatggtga cttggcac     180
actcagaagt tcaagggcaa ggccacattg actgcagata atcctccag cacagcctac    240
atgcaactca gcagcttgga atctgaggac tctgcggtct attactgtgc aagagaaagg   300
gataggttcg acgggtcctg gtttgcttac tggggccaag ggactctggt cactgtctct   360
gcagccaaaa cgacaccccc atctgtctat a                                  391
```

<210> SEQ ID NO 8
<211> LENGTH: 388
<212> TYPE: DNA
<213> ORGANISM: Artificial Sequence
<220> FEATURE:
<223> OTHER INFORMATION: synthetic monoclonal antibody M22-vh
      heavy-chain variable region

<400> SEQUENCE: 8
gaggtaaagc tgcaggagtc tggggctgag ctggtgaggc tggggcttc agtgaagctg    60
tcctgcaagg cttctggcta cacgttcacc acctactgga tgaactgggt taagcagagg   120
cctgagcaag gccttgagtg gattggaagg attgatcctt acgatagtga cactcactac   180
aatcaaaagt tcagtgacaa ggccatattg actgtagaca atcctccag cacagcctac    240
atgcaactca acagcctgac atctgaggac tctgcggtct attactgttc aaggggggac   300
tatgtcccca tctatgctat ggactactgg ggtcaaggaa cctcagtcac cgtctcctca   360
gccaaaacga cacccccatc tgtctata                                      388

<210> SEQ ID NO 9
<211> LENGTH: 388
<212> TYPE: DNA
<213> ORGANISM: Artificial Sequence
<220> FEATURE:
<223> OTHER INFORMATION: synthetic monoclonal antibody M28-vh
      heavy-chain variable region

<400> SEQUENCE: 9
gaggtgaagc tggaggagtc aggggctgag ctggtgaggc tggggcttc agtgaagctg    60
tcctgcaagg cttctggcta cacgttcacc acctactgga tgaactgggt taagcagagg   120
cctgagcaag gccttgagtg gattggaagg attgatcctt acgatagtga cactcactac   180
aatcaaaagt tcagtgacaa ggccatattg actgtagaca atcctccag cacagcctac    240
atgcaactca acagcctgac atctgaggac tctgcggtct attactgttc aaggggggac   300
tatgtcccca tctatgctat ggactactgg ggtcaaggaa cctcagtcac cgtctcctca   360
gccaaaacga cacccccatc tgtctata                                      388

<210> SEQ ID NO 10
<211> LENGTH: 364
<212> TYPE: DNA
<213> ORGANISM: Artificial Sequence
<220> FEATURE:
<223> OTHER INFORMATION: synthetic monoclonal antibody M13-vl
      light-chain variable region

<400> SEQUENCE: 10
gacattgtga tgacccagac tccactctcc ctgcctgtca gtcttggaga tcaagcctcc    60
atctcttgca gtctagtca gagcattgta catagtaatg gaaacaccta tttagaatgg   120
tacctgcaga aaccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggactt tattactgct ttcaaggttc acatgttccg   300
tggacgttcg gtggaggcac caagctggaa atcaaacggg ctgatgctgc accaactgta   360
tcca                                                                364

<210> SEQ ID NO 11
<211> LENGTH: 360
<212> TYPE: DNA
<213> ORGANISM: Artificial Sequence
<220> FEATURE:
<223> OTHER INFORMATION: synthetic monoclonal antibody M15-vl
      light-chain variable region

<400> SEQUENCE: 11

```
gacattgtga tgacacagac tccagcttct ttggctgtgt ctctagggca gagggccacc    60
atctcctgca aggccagcca agtgttgat tatgatggtg atagttatat gaactggtac    120
caacagaaac caggacagcc acccaaactc ctcatctatg ctgcatccaa tctagaatct    180
gggatcccag ccaggtttag tggcagtggg tctgggacag acttcatcct caacatccat    240
cctgtggagg aggaggatgc tgcaacctat cactgtcagc aaagtaatga ggatccgtgg    300
acgttcggtg gaggcaccaa gctggaaatc aaacgggctg atgctgcacc aactgtatcc    360
```

<210> SEQ ID NO 12
<211> LENGTH: 363
<212> TYPE: DNA
<213> ORGANISM: Artificial Sequence
<220> FEATURE:
<223> OTHER INFORMATION: synthetic monoclonal antibody M22-vl
    light-chain variable region

<400> SEQUENCE: 12

```
gatattgtga tgacccagac tccactctcc ctgcctgtca gtcttggaga tcaagcctcc    60
atctcttgca gatctagtca gagccttgta cacagtaatg aaacacccta tttacattgg    120
tacctgcaga ggccaggcca gtctccaaag ctcctgatct acaaagtttc caaccgattt    180
tctggggtcc cagacaggtt caatggcagt ggatcaggga cagatttcac actcaagatc    240
agcagagtgg aggctgagga tctgggaatt tatttctgct ctcaaagtac acatattcct    300
cggacgttcg gtggaggcac caagctggaa atcagacggg ctgatgctgc accaactgta    360
tcc                                                                  363
```

<210> SEQ ID NO 13
<211> LENGTH: 364
<212> TYPE: DNA
<213> ORGANISM: Artificial Sequence
<220> FEATURE:
<223> OTHER INFORMATION: synthetic monoclonal antibody M28-vl
    light-chain variable region

<400> SEQUENCE: 13

```
gatattgtga tcacacagtc tccactctcc ctgcctgtca gtcttggaga tcaagcctcc    60
atctcttgca gatctagtca gagccttgta cacagtaatg aaacacccta tttacattgg    120
tacctgcaga ggccaggcca gtctccaaag ctcctgatct acaaagtttc caaccgattt    180
tctggggtcc cagacaggtt caatggcagt ggatcaggga cagatttcac actcaagatc    240
agcagagtgg aggctgagga tctgggaatt tatttctgct ctcaaagtac acatattcct    300
cggacgttcg gtggaggcac caagctggaa atcagacggg ctgatgctgc accaactgta    360
tcca                                                                 364
```

<210> SEQ ID NO 14
<211> LENGTH: 132
<212> TYPE: PRT
<213> ORGANISM: Artificial Sequence
<220> FEATURE:
<223> OTHER INFORMATION: synthetic monoclonal antibody M13-vh
    heavy-chain variable region

<400> SEQUENCE: 14

```
Glu Val Gln Leu Glu Gln Ser Gly Ala Glu Leu Val Arg Pro Gly Ser
 1               5                  10                  15

Ser Val Lys Ile Ser Cys Lys Ala Ser Gly Tyr Val Phe Ser Thr Tyr
```

```
                    20                  25                  30

Trp Met Asn Trp Val Lys Gln Arg Pro Gly Gln Gly Leu Glu Trp Ile
            35                  40                  45

Gly Gln Ile Tyr Pro Gly Asp Gly Val Asn Tyr Asn Gly Glu Phe
        50                  55                  60

Lys Ala Arg Ala Thr Leu Thr Ala Asp Arg Ser Ser Thr Ala Tyr
 65                  70                  75                  80

Met Gln Leu Arg Ser Leu Thr Ser Glu Asp Ser Ala Val Tyr Phe Cys
                85                  90                  95

Ala Ser Ser Ser Tyr Tyr Gly Gly Ser Ser Val Ser Trp Leu Ala Tyr
            100                 105                 110

Trp Gly Gln Gly Thr Leu Val Ser Val Ser Ala Ala Lys Thr Thr Pro
        115                 120                 125

Pro Ser Val Tyr
        130

<210> SEQ ID NO 15
<211> LENGTH: 130
<212> TYPE: PRT
<213> ORGANISM: Artificial Sequence
<220> FEATURE:
<223> OTHER INFORMATION: synthetic monoclonal antibody M15-vh
      heavy-chain variable region

<400> SEQUENCE: 15

Glu Val Lys Leu Glu Glu Ser Gly Ala Glu Leu Ala Arg Pro Gly Ala
 1               5                  10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
            35                  40                  45

Gly Ala Ile Tyr Pro Gly Asp Gly Glu Thr Trp His Thr Gln Lys Phe
        50                  55                  60

Lys Gly Lys Ala Thr Leu Thr Ala Asp Lys Ser Ser Ser Thr Ala Tyr
 65                  70                  75                  80

Met Gln Leu Ser Ser Leu Glu Ser Glu Asp Ser Ala Val Tyr Tyr Cys
                85                  90                  95

Ala Arg Glu Arg Asp Arg Phe Asp Gly Ser Trp Phe Ala Tyr Trp Gly
            100                 105                 110

Gln Gly Thr Leu Val Thr Val Ser Ala Ala Lys Thr Thr Pro Pro Ser
        115                 120                 125

Val Tyr
    130

<210> SEQ ID NO 16
<211> LENGTH: 129
<212> TYPE: PRT
<213> ORGANISM: Artificial Sequence
<220> FEATURE:
<223> OTHER INFORMATION: synthetic monoclonal antibody M22-vh
      heavy-chain variable region

<400> SEQUENCE: 16

Glu Val Lys Leu Gln Glu Ser Gly Ala Glu Leu Val Arg Pro Gly Ala
 1               5                  10                  15

Ser Val Lys Leu Ser Cys Lys Ala Ser Gly Tyr Thr Phe Thr Thr Tyr
            20                  25                  30

Trp Met Asn Trp Val Lys Gln Arg Pro Glu Gln Gly Leu Glu Trp Ile
```

```
                35                  40                  45
Gly Arg Ile Asp Pro Tyr Asp Ser Asp Thr His Tyr Asn Gln Lys Phe
 50                  55                  60

Ser Asp Lys Ala Ile Leu Thr Val Asp Lys Ser Ser Thr Ala Tyr
 65                  70                  75                  80

Met Gln Leu Asn Ser Leu Thr Ser Glu Asp Ser Ala Val Tyr Tyr Cys
                 85                  90                  95

Ser Arg Gly Asp Tyr Val Pro Ile Tyr Ala Met Asp Tyr Trp Gly Gln
                100                 105                 110

Gly Thr Ser Val Thr Val Ser Ser Ala Lys Thr Thr Pro Pro Ser Val
                115                 120                 125

Tyr

<210> SEQ ID NO 17
<211> LENGTH: 129
<212> TYPE: PRT
<213> ORGANISM: Artificial Sequence
<220> FEATURE:
<223> OTHER INFORMATION: synthetic monoclonal antibody M28-vh
      heavy-chain variable region

<400> SEQUENCE: 17

Glu Val Lys Leu Glu Glu Ser Gly Ala Glu Leu Val Arg Pro Gly Ala
 1               5                  10                  15

Ser Val Lys Leu Ser Cys Lys Ala Ser Gly Tyr Thr Phe Thr Thr Tyr
                20                  25                  30

Trp Met Asn Trp Val Lys Gln Arg Pro Glu Gln Gly Leu Glu Trp Ile
                35                  40                  45

Gly Arg Ile Asp Pro Tyr Asp Ser Asp Thr His Tyr Asn Gln Lys Phe
 50                  55                  60

Ser Asp Lys Ala Ile Leu Thr Val Asp Lys Ser Ser Thr Ala Tyr
 65                  70                  75                  80

Met Gln Leu Asn Ser Leu Thr Ser Glu Asp Ser Ala Val Tyr Tyr Cys
                 85                  90                  95

Ser Arg Gly Asp Tyr Val Pro Ile Tyr Ala Met Asp Tyr Trp Gly Gln
                100                 105                 110

Gly Thr Ser Val Thr Val Ser Ser Ala Lys Thr Thr Pro Pro Ser Val
                115                 120                 125

Tyr

<210> SEQ ID NO 18
<211> LENGTH: 121
<212> TYPE: PRT
<213> ORGANISM: Artificial Sequence
<220> FEATURE:
<223> OTHER INFORMATION: synthetic monoclonal antibody M13-vl
      light-chain variable region

<400> SEQUENCE: 18

Asp Ile Val Met Thr Gln Thr Pro Leu Ser Leu Pro Val Ser Leu Gly
 1               5                  10                  15

Asp Gln Ala Ser Ile Ser Cys Lys Ser Ser Gln Ser Ile Val His Ser
                20                  25                  30

Asn Gly Asn Thr Tyr Leu Glu Trp Tyr Leu Gln Lys Pro Gly Gln Ser
                35                  40                  45

Pro Lys Leu Leu Ile Tyr Lys Val Ser Asn Arg Phe Ser Gly Val Pro
 50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Leu Gly Leu Tyr Tyr Cys Phe Gln Gly
                 85                  90                  95

Ser His Val Pro Trp Thr Phe Gly Gly Gly Thr Lys Leu Glu Ile Lys
            100                 105                 110

Arg Ala Asp Ala Ala Pro Thr Val Ser
        115                 120
```

<210> SEQ ID NO 19
<211> LENGTH: 120
<212> TYPE: PRT
<213> ORGANISM: Artificial Sequence
<220> FEATURE:
<223> OTHER INFORMATION: synthetic monoclonal antibody M15-vl
      light-chain variable region

<400> SEQUENCE: 19

```
Asp Ile Val Met Thr Gln Thr Pro Ala Ser Leu Ala Val Ser Leu Gly
  1               5                  10                  15

Gln Arg Ala Thr Ile Ser Cys Lys Ala Ser Gln Ser Val Asp Tyr Asp
                 20                  25                  30

Gly Asp Ser Tyr Met Asn Trp Tyr Gln Gln Lys Pro Gly Gln Pro Pro
            35                  40                  45

Lys Leu Leu Ile Tyr Ala Ala Ser Asn Leu Glu Ser Gly Ile Pro Ala
 50                  55                  60

Arg Phe Ser Gly Ser Gly Ser Gly Thr Asp Phe Ile Leu Asn Ile His
 65                  70                  75                  80

Pro Val Glu Glu Glu Asp Ala Ala Thr Tyr His Cys Gln Gln Ser Asn
                 85                  90                  95

Glu Asp Pro Trp Thr Phe Gly Gly Gly Thr Lys Leu Glu Ile Lys Arg
            100                 105                 110

Ala Asp Ala Ala Pro Thr Val Ser
        115                 120
```

<210> SEQ ID NO 20
<211> LENGTH: 121
<212> TYPE: PRT
<213> ORGANISM: Artificial Sequence
<220> FEATURE:
<223> OTHER INFORMATION: synthetic monoclonal antibody M22-vl
      light-chain variable region

<400> SEQUENCE: 20

```
Asp Ile Val Met Thr Gln Thr Pro Leu Ser Leu Pro Val Ser Leu Gly
  1               5                  10                  15

Asp Gln Ala Ser Ile Ser Cys Arg Ser Ser Gln Ser Leu Val His Ser
                 20                  25                  30

Asn Gly Asn Thr Tyr Leu His Trp Tyr Leu Gln Arg Pro Gly Gln Ser
            35                  40                  45

Pro Lys Leu Leu Ile Tyr Lys Val Ser Asn Arg Phe Ser Gly Val Pro
 50                  55                  60

Asp Arg Phe Asn Gly Ser Gly Ser Gly Thr Asp Phe Thr Leu Lys Ile
 65                  70                  75                  80

Ser Arg Val Glu Ala Glu Asp Leu Gly Ile Tyr Phe Cys Ser Gln Ser
                 85                  90                  95

Thr His Ile Pro Arg Thr Phe Gly Gly Gly Thr Lys Leu Glu Ile Arg
            100                 105                 110
```

Arg Ala Asp Ala Ala Pro Thr Val Ser
        115                 120

<210> SEQ ID NO 21
<211> LENGTH: 121
<212> TYPE: PRT
<213> ORGANISM: Artificial Sequence
<220> FEATURE:
<223> OTHER INFORMATION: synthetic monoclonal antibody M28-vl
      light-chain variable region

<400> SEQUENCE: 21

Asp Ile Val Ile Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Arg Pro Gly Gln Ser
        35                  40                  45

Pro Lys Leu Leu Ile Tyr Lys Val Ser Asn Arg Phe Ser Gly Val Pro
    50                  55                  60

Asp Arg Phe Asn Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Ser
                85                  90                  95

Thr His Ile Pro Arg Thr Phe Gly Gly Gly Thr Lys Leu Glu Ile Arg
            100                 105                 110

Arg Ala Asp Ala Ala Pro Thr Val Ser
        115                 120

<210> SEQ ID NO 22
<211> LENGTH: 5
<212> TYPE: PRT
<213> ORGANISM: Artificial Sequence
<220> FEATURE:
<223> OTHER INFORMATION: synthetic monoclonal antibody M13-vh
      heavy-chain complementary determining region 1 (CDR1)

<400> SEQUENCE: 22

Thr Tyr Trp Met Asn
1               5

<210> SEQ ID NO 23
<211> LENGTH: 17
<212> TYPE: PRT
<213> ORGANISM: Artificial Sequence
<220> FEATURE:
<223> OTHER INFORMATION: synthetic monoclonal antibody M13-vh
      heavy-chain complementary determining region 2 (CDR2)

<400> SEQUENCE: 23

Gln Ile Tyr Pro Gly Asp Gly Gly Val Asn Tyr Asn Gly Glu Phe Lys
1               5                   10                  15

Ala

<210> SEQ ID NO 24
<211> LENGTH: 14
<212> TYPE: PRT
<213> ORGANISM: Artificial Sequence
<220> FEATURE:
<223> OTHER INFORMATION: synthetic monoclonal antibody M13-vh
      heavy-chain complementary determining region 3 (CDR3)

<400> SEQUENCE: 24

```
Ser Ser Tyr Tyr Gly Gly Ser Ser Val Ser Trp Leu Ala Tyr
 1               5                  10
```

<210> SEQ ID NO 25
<211> LENGTH: 16
<212> TYPE: PRT
<213> ORGANISM: Artificial Sequence
<220> FEATURE:
<223> OTHER INFORMATION: synthetic monoclonal antibody M13-vl
      light-chain complementary determining region 1 (CDR1)

<400> SEQUENCE: 25

```
Lys Ser Ser Gln Ser Ile Val His Ser Asn Gly Asn Thr Tyr Leu Glu
 1               5                  10                  15
```

<210> SEQ ID NO 26
<211> LENGTH: 6
<212> TYPE: PRT
<213> ORGANISM: Artificial Sequence
<220> FEATURE:
<223> OTHER INFORMATION: synthetic monoclonal antibody M13-vl
      light-chain complementary determining region 2 (CDR2)

<400> SEQUENCE: 26

```
Lys Val Ser Asn Arg Phe
 1               5
```

<210> SEQ ID NO 27
<211> LENGTH: 9
<212> TYPE: PRT
<213> ORGANISM: Artificial Sequence
<220> FEATURE:
<223> OTHER INFORMATION: synthetic monoclonal antibody M13-vl
      light-chain complementary determining region 3 (CDR3)

<400> SEQUENCE: 27

```
Phe Gln Gly Ser His Val Pro Trp Thr
 1               5
```

<210> SEQ ID NO 28
<211> LENGTH: 5
<212> TYPE: PRT
<213> ORGANISM: Artificial Sequence
<220> FEATURE:
<223> OTHER INFORMATION: synthetic monoclonal antibody M15-vh
      heavy-chain complementary determining region 1 (CDR1)

<400> SEQUENCE: 28

```
Ser Tyr Trp Met Gln
 1               5
```

<210> SEQ ID NO 29
<211> LENGTH: 17
<212> TYPE: PRT
<213> ORGANISM: Artificial Sequence
<220> FEATURE:
<223> OTHER INFORMATION: synthetic monoclonal antibody M15-vh
      heavy-chain complementary determining region 2 (CDR2)

<400> SEQUENCE: 29

```
Ala Ile Tyr Pro Gly Asp Gly Glu Thr Trp His Thr Gln Lys Phe Lys
 1               5                  10                  15
Gly
```

<210> SEQ ID NO 30
<211> LENGTH: 12
<212> TYPE: PRT

```
<213> ORGANISM: Artificial Sequence
<220> FEATURE:
<223> OTHER INFORMATION: synthetic monoclonal antibody M15-vh
      heavy-chain complementary determining region 3 (CDR3)

<400> SEQUENCE: 30

Glu Arg Asp Arg Phe Asp Gly Ser Trp Phe Ala Tyr
1               5                   10

<210> SEQ ID NO 31
<211> LENGTH: 15
<212> TYPE: PRT
<213> ORGANISM: Artificial Sequence
<220> FEATURE:
<223> OTHER INFORMATION: synthetic monoclonal antibody M15-vl
      light-chain complementary determining region 1 (CDR1)

<400> SEQUENCE: 31

Lys Ala Ser Gln Ser Val Asp Tyr Asp Gly Asp Ser Tyr Met Asn
1               5                   10                  15

<210> SEQ ID NO 32
<211> LENGTH: 7
<212> TYPE: PRT
<213> ORGANISM: Artificial Sequence
<220> FEATURE:
<223> OTHER INFORMATION: synthetic monoclonal antibody M15-vl
      light-chain complementary determining region 2 (CDR2)

<400> SEQUENCE: 32

Ala Ala Ser Asn Leu Glu Ser
1               5

<210> SEQ ID NO 33
<211> LENGTH: 9
<212> TYPE: PRT
<213> ORGANISM: Artificial Sequence
<220> FEATURE:
<223> OTHER INFORMATION: synthetic monoclonal antibody M15-vl
      light-chain complementary determining region 3 (CDR3)

<400> SEQUENCE: 33

Gln Gln Ser Asn Glu Asp Pro Trp Thr
1               5

<210> SEQ ID NO 34
<211> LENGTH: 5
<212> TYPE: PRT
<213> ORGANISM: Artificial Sequence
<220> FEATURE:
<223> OTHER INFORMATION: synthetic monoclonal antibody M22-vh
      heavy-chain complementary determining region 1 (CDR1)

<400> SEQUENCE: 34

Thr Tyr Trp Met Asn
1               5

<210> SEQ ID NO 35
<211> LENGTH: 17
<212> TYPE: PRT
<213> ORGANISM: Artificial Sequence
<220> FEATURE:
<223> OTHER INFORMATION: synthetic monoclonal antibody M22-vh
      heavy-chain complementary determining region 2 (CDR2)

<400> SEQUENCE: 35

Arg Ile Asp Pro Tyr Asp Ser Asp Thr His Tyr Asn Gln Lys Phe Ser
1               5                   10                  15
```

Asp

<210> SEQ ID NO 36
<211> LENGTH: 11
<212> TYPE: PRT
<213> ORGANISM: Artificial Sequence
<220> FEATURE:
<223> OTHER INFORMATION: synthetic monoclonal antibody M22-vh
      heavy-chain complementary determining region 3 (CDR3)

<400> SEQUENCE: 36

Gly Asp Tyr Val Pro Ile Tyr Ala Met Asp Tyr
1               5                   10

<210> SEQ ID NO 37
<211> LENGTH: 16
<212> TYPE: PRT
<213> ORGANISM: Artificial Sequence
<220> FEATURE:
<223> OTHER INFORMATION: synthetic monoclonal antibody M22-vl
      light-chain complementary determining region 1 (CDR1)

<400> SEQUENCE: 37

Arg Ser Ser Gln Ser Leu Val His Ser Asn Gly Asn Thr Tyr Leu His
1               5                   10                  15

<210> SEQ ID NO 38
<211> LENGTH: 7
<212> TYPE: PRT
<213> ORGANISM: Artificial Sequence
<220> FEATURE:
<223> OTHER INFORMATION: synthetic monoclonal antibody M22-vl
      light-chain complementary determining region 2 (CDR2)

<400> SEQUENCE: 38

Lys Val Ser Asn Arg Phe Ser
1               5

<210> SEQ ID NO 39
<211> LENGTH: 8
<212> TYPE: PRT
<213> ORGANISM: Artificial Sequence
<220> FEATURE:
<223> OTHER INFORMATION: synthetic monoclonal antibody M22-vl
      light-chain complementary determining region 3 (CDR3)

<400> SEQUENCE: 39

Ser Gln Ser Thr His Ile Pro Arg
1               5

<210> SEQ ID NO 40
<211> LENGTH: 5
<212> TYPE: PRT
<213> ORGANISM: Artificial Sequence
<220> FEATURE:
<223> OTHER INFORMATION: synthetic monoclonal antibody M28-vh
      heavy-chain complementary determining region 1 (CDR1)

<400> SEQUENCE: 40

Thr Tyr Trp Met Asn
1               5

<210> SEQ ID NO 41
<211> LENGTH: 17
<212> TYPE: PRT
<213> ORGANISM: Artificial Sequence
<220> FEATURE:

```
<223> OTHER INFORMATION: synthetic monoclonal antibody M28-vh
      heavy-chain complementary determining region 2 (CDR2)

<400> SEQUENCE: 41

Arg Ile Asp Pro Tyr Asp Ser Asp Thr His Tyr Asn Gln Lys Phe Ser
1               5                   10                  15

Asp

<210> SEQ ID NO 42
<211> LENGTH: 11
<212> TYPE: PRT
<213> ORGANISM: Artificial Sequence
<220> FEATURE:
<223> OTHER INFORMATION: synthetic monoclonal antibody M28-vh
      heavy-chain complementary determining region 3 (CDR3)

<400> SEQUENCE: 42

Gly Asp Tyr Val Pro Ile Tyr Ala Met Asp Tyr
1               5                   10

<210> SEQ ID NO 43
<211> LENGTH: 16
<212> TYPE: PRT
<213> ORGANISM: Artificial Sequence
<220> FEATURE:
<223> OTHER INFORMATION: synthetic monoclonal antibody M28-vl
      light-chain complementary determining region 1 (CDR1)

<400> SEQUENCE: 43

Arg Ser Ser Gln Ser Leu Val His Ser Asn Gly Asn Thr Tyr Leu His
1               5                   10                  15

<210> SEQ ID NO 44
<211> LENGTH: 7
<212> TYPE: PRT
<213> ORGANISM: Artificial Sequence
<220> FEATURE:
<223> OTHER INFORMATION: synthetic monoclonal antibody M28-vl
      light-chain complementary determining region 2 (CDR2)

<400> SEQUENCE: 44

Lys Val Ser Asn Arg Phe Ser
1               5

<210> SEQ ID NO 45
<211> LENGTH: 8
<212> TYPE: PRT
<213> ORGANISM: Artificial Sequence
<220> FEATURE:
<223> OTHER INFORMATION: synthetic monoclonal antibody M28-vl
      light-chain complementary determining region 3 (CDR3)

<400> SEQUENCE: 45

Ser Gln Ser Thr His Ile Pro Arg
1               5

<210> SEQ ID NO 46
<211> LENGTH: 6
<212> TYPE: PRT
<213> ORGANISM: Artificial Sequence
<220> FEATURE:
<223> OTHER INFORMATION: synthetic 6-His tag, metal chelate affinity
      tag, polyhistidine tag, six adjacent histidines

<400> SEQUENCE: 46

His His His His His His
1               5
```

```
<210> SEQ ID NO 47
<211> LENGTH: 8
<212> TYPE: PRT
<213> ORGANISM: Artificial Sequence
<220> FEATURE:
<223> OTHER INFORMATION: synthetic anti-DYKDDDDK epitope tag

<400> SEQUENCE: 47

Asp Tyr Lys Asp Asp Asp Asp Lys
 1               5
```

METHODS AND COMPOSITIONS FOR IMPROVING EFFICIENCY OF NUCLEIC ACIDS AMPLIFICATION REACTIONS

CROSS-REFERENCES TO RELATED APPLICATIONS

The present application is a continuation of U.S. patent application Ser. No. 12/683,950, filed Jan. 7, 2010, which claims benefit of priority to U.S. Provisional Patent Application No. 61/143,350, filed Jan. 8, 2009, each is incorporated by reference in its entirety for all purposes.

REFERENCE TO SUBMISSION OF A SEQUENCE LISTING AS A TEXT FILE

The Sequence Listing written in file SEQTXT_94260-914131.txt, created on Sep. 10, 2014, 34,260 bytes, machine format IBM-PC, MS-Windows operating system, is hereby incorporated by reference.

FIELD OF THE INVENTION

The present invention relates to nucleic acid amplification reactions. The present invention encompasses hybrid polymerases with improved processivity as well as methods and compositions for reducing non-specific amplification during reactions such as PCR.

BACKGROUND OF THE INVENTION

Nucleic acid amplification reactions, such as polymerase chain reaction (PCR), are generally template-dependent reactions in which a desired nucleic acid sequence is amplified by treating separate complementary strands of a target nucleic acid with an excess of two oligonucleotide primers. The primers are extended to form complementary primer extension products which act as templates for synthesizing the desired nucleic acid sequence. In such processes, the nucleic acid sequence between the primers on the respective DNA strands is selectively amplified.

BRIEF SUMMARY OF THE INVENTION

Accordingly, the present invention provides methods and compositions for improving the efficiency and the specificity of nucleic acid synthesis and amplification reactions.

In one aspect, the present invention provides a method of amplifying a target nucleic acid. This method includes incubating the target nucleic acid with a reaction mixture that includes at least one primer, a hybrid polymerase, and an osmolyte. In a further aspect, the incubating step is conducted under conditions that permit amplification of the target nucleic acid by the hybrid polymerase. In a still further aspect, the hybrid polymerase comprises a polymerase domain and a DNA binding domain.

In a further aspect, the invention provides a kit for quantitative PCR. In an exemplary aspect, the kit includes: a hybrid polymerase with reduced exonuclease activity, dNTPs, a buffer that includes sarcosine, and directions for using the hybrid polymerase in a nucleic acid amplification reaction.

In some embodiments, the invention provides for a method of amplifying a target nucleic acid in a sample. In some embodiments, the method comprises incubating said target nucleic acid in a reaction mixture comprising:
  at least one primer,
  a hybrid polymerase comprising a polymerase domain and a heterologous DNA binding domain, and
  an additive selected from the group consisting of sarcosine and heparin, in a sufficient amount to improve efficiency of the amplification reaction by at least 10% compared to a reaction mixture lacking the additive,
wherein said incubating is under conditions that permit amplification of said target nucleic acid by said hybrid polymerase.

In some embodiments, the additive is sarcosine, which is at a concentration of less than 600 mM.

In some embodiments, the hybrid polymerase comprises a mutation in an exonuclease domain such that the polymerase substantially lacks a 3'-5' exonuclease activity. In some embodiments, the hybrid polymerase comprises a Family B-like polymerase that substantially lacks (e.g., has a mutation resulting in a substantial lack of) a 3'-5' exonuclease activity. In some embodiments, the hybrid polymerase comprises a polypeptide sequence that is substantially identical to SEQ ID NO:2, i.e., is at least 65%, 70%, 75%, 80%, 85%, 90%, 91%, 92%, 93%, 94%, 95%, 96%, 97%, 98% or 99% or greater amino acid sequence identity across the polymerase domain (i.e., all but SEQ ID NO:3) or the entire sequence of SEQ ID NO:2. In some embodiments, the hybrid polymerase comprises SEQ ID NO:2.

In some embodiments, the sample comprises an amplification inhibitor and wherein an aliquot of the sample is added to the reaction mixture in an amount such that the inhibitor is at a concentration capable of inhibiting wildtype Taq polymerase and wherein the hybrid polymerase amplifies the target nucleic acid. In some embodiments, the sample is selected from blood or intact cells or food samples.

In some embodiments, the hybrid polymerase is complexed with one or more antibodies prior to a heating step during the incubating step. In some embodiments, the antibody comprises a heavy chain variable region and a light chain variable region, wherein the variable regions comprise complementary determining regions (CDRs), wherein:
  (a) the heavy chain variable region CDRs comprise SEQ ID NO:22, SEQ ID NO:23, and SEQ ID NO:24, and the light chain variable region CDRs comprise SEQ ID NO:25, SEQ ID NO:26, and SEQ ID NO:27; or
  (b) the heavy chain variable region CDRs comprise SEQ ID NO:28, SEQ ID NO:29, and SEQ ID NO:30, and the light chain variable region CDRs comprise SEQ ID NO:31, SEQ ID NO:32, and SEQ ID NO:33; or
  (c) the heavy chain variable region CDRs comprise SEQ ID NO:34, SEQ ID NO:35, and SEQ ID NO:36, and the light chain variable region CDRs comprise SEQ ID NO:37, SEQ ID NO:38, and SEQ ID NO:39.

In some embodiments, signal from the amplification is detected in real-time.

In some embodiments, the heterologous DNA binding domain is substantially identical to (i.e., at least 65%, 70%, 75%, 80%, 85%, 90%, 91%, 92%, 93%, 94%, 95%, 96%, 97%, 98% or 99% or greater) to SEQ ID NO:3.

In some embodiments, the amplification reaction is performed with extension times of less than 1, 2, 3, or 4 seconds.

In some embodiments, the polymerase and exonuclease domains are from a Family B DNA polymerase.

In some embodiments, the reaction mixture further comprises a double-stranded DNA binding dye.

The present invention also provides for reaction mixtures. In some embodiments, the reaction mixture comprises:
a hybrid polymerase, wherein said polymerase comprises a polymerase domain and a heterologous DNA binding domain; and
an additive selected from the group consisting of sarcosine and heparin, in a sufficient amount to improve efficiency of the amplification reaction by at least 10% compared to a reaction mixture lacking the additive.

In some embodiments, the reaction mixture further comprises at least one oligonucleotide primer.

In some embodiments, the additive is sarcosine, which is at a concentration of less than 600 mM.

In some embodiments, the hybrid polymerase comprises a mutation in an exonuclease domain such that the polymerase substantially lacks a 3'-5' exonuclease activity. In some embodiments, the hybrid polymerase comprises a Family B-like polymerase that substantially lacks (e.g., has a mutation resulting in a substantial lack of) a 3'-5' exonuclease activity. In some embodiments, the hybrid polymerase comprises a polypeptide sequence that is substantially identical to SEQ ID NO:2, i.e., is at least 65%, 70%, 75%, 80%, 85%, 90%, 91%, 92%, 93%, 94%, 95%, 96%, 97%, 98% or 99% or greater amino acid sequence identity across the polymerase domain (i.e., all but SEQ ID NO:3) or the entire sequence of SEQ ID NO:2. In some embodiments, the polymerase comprises SEQ ID NO:2.

In some embodiments, the mixture comprises an aliquot of a sample, wherein said sample comprises an amplification inhibitor, wherein the inhibitor is at a concentration capable of inhibiting wildtype Taq polymerase. In some embodiments, the sample is selected from blood or intact cells or food samples.

In some embodiments, the hybrid polymerase is complexed with an antibody.

In some embodiments, the antibody comprises a heavy chain variable region and a light chain variable region, wherein the variable regions comprise complementary determining regions (CDRs), wherein:
(a) the heavy chain variable region CDRs comprise SEQ ID NO:22, SEQ ID NO:23, and SEQ ID NO:24, and the light chain variable region CDRs comprise SEQ ID NO:25, SEQ ID NO:26, and SEQ ID NO:27; or
(b) the heavy chain variable region CDRs comprise SEQ ID NO:28, SEQ ID NO:29, and SEQ ID NO:30, and the light chain variable region CDRs comprise SEQ ID NO:31, SEQ ID NO:32, and SEQ ID NO:33; or
(c) the heavy chain variable region CDRs comprise SEQ ID NO:34, SEQ ID NO:35, and SEQ ID NO:36, and the light chain variable region CDRs comprise SEQ ID NO:37, SEQ ID NO:38, and SEQ ID NO:39.

In some embodiments, the heterologous DNA binding domain is substantially identical to (i.e., at least 65%, 70%, 75%, 80%, 85%, 90%, 91%, 92%, 93%, 94%, 95%, 96%, 97%, 98% or 99% or greater) to SEQ ID NO:3.

In some embodiments, the polymerase and exonuclease domains are from a Family B DNA polymerase.

In some embodiments, the reaction mixture comprises one or more different deoxyribonucleotide triphosphates.

In some embodiments, the reaction mixture further comprises a double-stranded DNA binding dye.

The present invention also provides kits. In some embodiments, the kit comprises:
a hybrid polymerase comprising a polymerase domain and a heterologous DNA binding domain; and
an additive selected from the group consisting of sarcosine and heparin, in a sufficient amount to improve efficiency of an amplification reaction by at least 10% compared to a reaction mixture lacking the additive.

In some embodiments, the hybrid polymerase comprises a mutation in an exonuclease domain such that the polymerase substantially lacks a 3'-5' exonuclease activity. In some embodiments, the hybrid polymerase comprises a Family B-like polymerase that substantially lacks (e.g., has a mutation resulting in a substantial lack of) a 3'-5' exonuclease activity. In some embodiments, the hybrid polymerase comprises a polypeptide sequence that is substantially identical to SEQ ID NO:2, i.e., is at least 65%, 70%, 75%, 80%, 85%, 90%, 91%, 92%, 93%, 94%, 95%, 96%, 97%, 98% or 99% or greater amino acid sequence identity across the polymerase domain (i.e., all but SEQ ID NO:3) or the entire sequence of SEQ ID NO:2. In some embodiments, the hybrid polymerase comprise SEQ ID NO:2.

In some embodiments, the kit further comprises an antibody that is specific for the hybrid polymerase.

In some embodiments, the antibody comprises a heavy chain variable region and a light chain variable region, wherein the variable regions comprise complementary determining regions (CDRs), wherein:
(a) the heavy chain variable region CDRs comprise SEQ ID NO:22, SEQ ID NO:23, and SEQ ID NO:24, and the light chain variable region CDRs comprise SEQ ID NO:25, SEQ ID NO:26, and SEQ ID NO:27; or
(b) the heavy chain variable region CDRs comprise SEQ ID NO:28, SEQ ID NO:29, and SEQ ID NO:30, and the light chain variable region CDRs comprise SEQ ID NO:31, SEQ ID NO:32, and SEQ ID NO:33; or
(c) the heavy chain variable region CDRs comprise SEQ ID NO:34, SEQ ID NO:35, and SEQ ID NO:36, and the light chain variable region CDRs comprise SEQ ID NO:37, SEQ ID NO:38, and SEQ ID NO:39.

In some embodiments, the heterologous DNA binding domain is substantially identical to (i.e., at least 65%, 70%, 75%, 80%, 85%, 90%, 91%, 92%, 93%, 94%, 95%, 96%, 97%, 98% or 99% or greater) to SEQ ID NO:3.

In some embodiments, the polymerase and exonuclease domains are from a Family B DNA polymerase.

In some embodiments, the kit further comprises one or more of:
one or more different deoxyribonucleotide triphosphates;
a double-stranded DNA binding dye; and
an oligonucleotide primer.

The present invention also provides for an isolated antibody having binding specificity for a protein consisting of SEQ ID NO:2, wherein the antibody comprises a heavy chain and a light chain variable region, wherein the variable regions comprise complementary determining regions (CDRs), wherein:
(a) the heavy chain variable region CDRs comprise SEQ ID NO:22, SEQ ID NO:23, and SEQ ID NO:24, and the light chain variable region CDRs comprise SEQ ID NO:25, SEQ ID NO:26, and SEQ ID NO:27; or
(b) the heavy chain variable region CDRs comprise SEQ ID NO:28, SEQ ID NO:29, and SEQ ID NO:30, and the light chain variable region CDRs comprise SEQ ID NO:31, SEQ ID NO:32, and SEQ ID NO:33; or
(c) the heavy chain variable region CDRs comprise SEQ ID NO:34, SEQ ID NO:35, and SEQ ID NO:36, and the light chain variable region CDRs comprise SEQ ID NO:37, SEQ ID NO:38, and SEQ ID NO:39.

In some embodiments, the heavy chain and light chain variable regions comprise:
(a) SEQ ID NO:14 and SEQ ID NO:18, respectively;
(b) SEQ ID NO:15 and SEQ ID NO:19, respectively;

(c) SEQ ID NO:16 and SEQ ID NO:20, respectively; or
(d) SEQ ID NO:17 and SEQ ID NO:21, respectively;

The present invention also provides for an isolated polynucleotide encoding a polypeptide comprising a heavy chain or light chain variable region as discussed above.

The present invention also provides for an antibody complexed with a polymerase, wherein the antibody comprises a heavy chain and/or light chain variable region as discussed above.

BRIEF DESCRIPTION OF THE DRAWINGS

FIG. 4A shows the amino acid sequence of an exemplary hybrid polymerases that includes a DNA binding domain (SEQ ID NO:2). FIG. 4B shows the amino acid sequence of an exemplary DNA binding domain (SEQ ID NO:3).

DETAILED DESCRIPTION OF THE PREFERRED EMBODIMENTS

Figure 1:
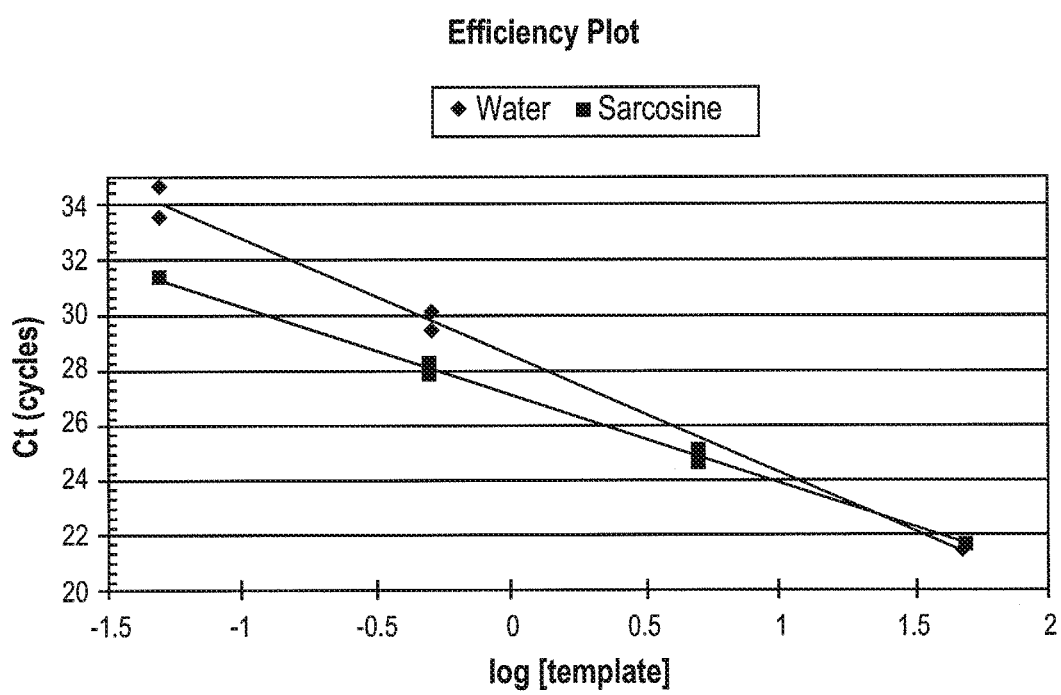
FIG. 1 shows the effect of sarcosine on efficiency of a qPCR reaction

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention. It will be apparent to one of skill in the art that these additional features are also encompassed by the present invention.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

The term "hybrid polymerase" is used herein to describe a polymerase that comprises amino acid residues from multiple parent sequences. Hybrid polymerases may comprise both polymerase domains as well as DNA binding domains.

The term "hybrid position" refers to a position that differs between parent sequences, or subsequences.

A "wild type polymerase" refers to a naturally occurring polymerase. A "wild type polymerase amino acid sequence" refers to the naturally occurring amino acid sequence.

A "native" polymerase sequence refers to a parent polymerase sequence, typically a "wildtype" sequence.

A "parent polymerase sequence" indicates a starting or reference amino acid or nucleic acid sequence prior to a manipulation of the invention. The term is used interchangeably with "starting sequence". Parent sequences may be wild-type proteins, proteins containing mutations, or other engineered proteins. Parent sequences can also be full-length proteins, protein subunits, protein domains, amino acid motifs, protein active sites, or any polymerase sequence or subset of polymerase sequences, whether continuous or interrupted by other polypeptide sequences.

The term "DNA binding domain" refers to a protein domain that binds DNA in a sequence non-specific manner. In some embodiments, the DNA binding domain is a protein domain which binds with significant affinity to DNA, for which there is no known nucleic acid which binds to the protein domain with more than 100-fold more affinity than another nucleic acid with the same nucleotide composition but a different nucleotide sequence.

The term "Sso7d" or "Sso7d DNA binding domain" or "Sso7d-like DNA binding domain" or "Sso7d binding protein" refers to nucleic acid and polypeptide polymorphic variants, alleles, mutants, and interspecies homologs that: (1) have an amino acid sequence that has greater than about 60% amino acid sequence identity, 65%, 70%, 75%, 80%, 85%, 90%, 91%, 92%, 93%, 94%, 95%, 96%, 97%, 98% or 99% or greater amino acid sequence identity, preferably over a region of at least about 15, 25, 35, 50, or 63 amino acids, to an Sso7d sequence of SEQ ID NO: 3; 2) bind to antibodies, e.g., polyclonal antibodies, raised against an immunogen comprising an amino acid sequence of SEQ ID NO: 3 and conservatively modified variants thereof; (3) specifically hybridize under stringent hybridization conditions to a Sso7d nucleic acid sequence of SEQ ID NO: 3 and conservatively modified variants thereof; or (4) have a nucleic acid sequence that has greater than about 90%, 91%, 92%, 93%, 94%, 95%, 96%, 97%, 98%, 99%, or higher nucleotide sequence identity, preferably over a region of at least about 50, 100, 150, or more nucleotides, to SEQ ID NO:4. The term includes both full-length Sso7d polypeptides and fragments of the polypeptides that have sequence non-specific double-stranded binding activity. Sso7d-like proteins include Sac7d and Sac7e.

"Domain" refers to a unit of a protein or protein complex, comprising a polypeptide subsequence, a complete polypeptide sequence, or a plurality of polypeptide sequences where that unit has a defined function. The function is understood to be broadly defined and can be ligand binding, catalytic activity or can have a stabilizing effect on the structure of the protein.

"Efficiency" in the context of a reaction of this invention refers to the ability of the components of the reaction to perform their functions under specific reaction conditions. For example, efficiency may refer to the ability of a polymerase enzyme to perform its catalytic function under specific reaction conditions. Methods for calculating efficiency of amplification reactions are known in the art and described in further detail herein.

"Enhances" in the context of an enzyme refers to improving the activity of the enzyme, i.e., increasing the amount of product per unit enzyme per unit time.

"Heterologous", when used with reference to portions of a protein, indicates that the protein comprises two or more domains that are not found in the same relationship to each other in nature. Such a protein, e.g., a fusion protein, contains two or more domains from unrelated proteins arranged to make a new functional protein.

"Join" refers to any method known in the art for functionally connecting protein domains, including without limitation recombinant fusion with or without intervening domains, intein-mediated fusion, non-covalent association, and covalent bonding, including disulfide bonding; hydrogen bonding; electrostatic bonding; and conformational bonding, e.g., antibody-antigen, and biotin-avidin associations.

"Polymerase" refers to an enzyme that performs template-directed synthesis of polynucleotides. The term encompasses both the full length polypeptide and a domain that has polymerase activity.

"Processivity" refers to the ability of a polymerase to remain bound to the template or substrate and perform polynucleotide synthesis. Processivity is measured by the number of catalytic events (e.g., nucleotides incorporated) that take place per binding event.

"Thermally stable polymerase" as used herein refers to any enzyme that catalyzes polynucleotide synthesis by addition of nucleotide units to a nucleotide chain using DNA or RNA as a template and has an optimal activity at a temperature above 45° C.

"Thermus polymerase" refers to a family A DNA polymerase isolated from any Thermus species, including without limitation Thermus aquaticus, Thermus brockianus, and Thermus thermophilus; any recombinant polymerases deriving from Thermus species, and any functional derivatives thereof, whether derived by genetic modification or chemical modification or other methods known in the art.

The term "amplification reaction" refers to any in vitro means for multiplying the copies of a target sequence of nucleic acid. Such methods include but are not limited to polymerase chain reaction (PCR), DNA ligase chain reaction (see U.S. Pat. Nos. 4,683,195 and 4,683,202; PCR Protocols: A Guide to Methods and Applications (Innis et al., eds, 1990)), (LCR), QBeta RNA replicase, and RNA transcription-based (such as TAS and 3SR) amplification reactions as well as others known to those of skill in the art.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term "amplifying" typically refers to an "exponential" increase in target nucleic acid. However, "amplifying" as used herein can also refer to linear increases in the numbers of a select target sequence of nucleic acid, such as is obtained with cycle sequencing.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. As discussed further herein, amplification reaction mixtures may also further include stabilizers and other additives to optimize efficiency and specificity. Depending upon the context, the mixture can be either a complete or incomplete amplification reaction mixture "Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

"Long PCR" refers to the amplification of a DNA fragment of 5 kb or more in length. Long PCR is typically performed using specially-adapted polymerases or polymerase mixtures (see, e.g., U.S. Pat. Nos. 5,436,149 and 5,512,462) that are distinct from the polymerases conventionally used to amplify shorter products.

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., Innis et al., supra.

A "temperature profile" refers to the temperature and lengths of time of the denaturation, annealing and/or extension steps of a PCR or cycle sequencing reaction. A temperature profile for a PCR or cycle sequencing reaction typically consists of 10 to 60 repetitions of similar or identical shorter temperature profiles; each of these shorter profiles may typically define a two step or three-step cycle. Selection of a temperature profile is based on various considerations known to those of skill in the art, see, e.g., Innis et al., supra. In a long PCR reaction as described herein, the extension time required to obtain an amplification product of 5 kb or greater in length is reduced compared to conventional polymerase mixtures.

PCR "sensitivity" refers to the ability to amplify a target nucleic acid that is present in low copy number. "Low copy number" refers to $10^5$, often $10^4$, $10^3$, $10^2$, $10^1$ or fewer, copies of the target sequence in the nucleic acid sample to be amplified.

The term "polymerase primer/template binding specificity" as used herein refers to the ability of a polymerase to discriminate between correctly matched primer/templates and mismatched primer templates. An "increase in polymerase primer/template binding specificity" in this context refers to an increased ability of a polymerase of the invention to discriminate between matched primer/template and mismatched primer complexes in comparison to a wild type polymerase.

A "template" refers to a polynucleotide sequence that comprises the polynucleotide to be amplified, flanked by primer hybridization sites. Thus, a "target template" comprises the target polynucleotide sequence flanked by hybridization sites for a 5' primer and a 3' primer.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a fluorophore (e.g., quantum dot) or another moiety.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine. Amino acid analogs refers to compounds that have the same basic chemical structure as a naturally occurring amino acid, i.e., a carbon atom that is bound to a hydrogen atom, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The term "encoding" refers to a polynucleotide sequence encoding one or more amino acids. The term does not require a start or stop codon. An amino acid sequence can be encoded in any one of six different reading frames provided by a polynucleotide sequence.

The term "promoter" refers to regions or sequence located upstream and/or downstream from the start of transcription and which are involved in recognition and binding of RNA polymerase and other proteins to initiate transcription.

A "vector" refers to a polynucleotide, which when independent of the host chromosome, is capable replication in a host organism. Preferred vectors include plasmids and typically have an origin of replication. Vectors can comprise, e.g., transcription and translation terminators, transcription and translation initiation sequences, and promoters useful for regulation of the expression of the particular nucleic acid.

"Recombinant" refers to a human manipulated polynucleotide or a copy or complement of a human manipulated polynucleotide. For instance, a recombinant expression cassette comprising a promoter operably linked to a second polynucleotide may include a promoter that is heterologous to the second polynucleotide as the result of human manipulation (e.g., by methods described in Sambrook et al., Molecular Cloning—A Laboratory Manual, Cold Spring Harbor Laboratory, Cold Spring Harbor, N.Y., (1989) or Current Protocols in Molecular Biology Volumes 1-3, John Wiley & Sons, Inc. (1994-1998)) of an isolated nucleic acid comprising the expression cassette. In another example, a recombinant expression cassette may comprise polynucleotides combined in such a way that the polynucleotides are extremely unlikely to be found in nature. For instance, human manipulated restriction sites or plasmid vector sequences may flank or separate the promoter from the second polynucleotide. One of skill will recognize that polynucleotides can be manipulated in many ways and are not limited to the examples above.

A "polymerase polypeptide" of the present invention is a protein comprising a polymerase domain. The polymerase polypeptide may also comprise additional domains including a heterologous DNA binding domain, e.g., Sso7D. DNA polymerases are well-known to those skilled in the art, including but not limited to DNA polymerases isolated or derived from *Pyrococcus furiosus*, *Thermococcus litoralis*, and *Thermotoga maritime*, or modified versions there of. They include both DNA-dependent polymerases and RNA-dependent polymerases such as reverse transcriptase. At least five families of DNA-dependent DNA polymerases are known, although most fall into families A, B and C. There is little or no sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, δ, and ε, are implicated in nuclear replication, and a family A polymerase, polymerase γ, is used for mitochondrial DNA replication. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

Polypeptide polymerases of the present invention have polymerase activity. Using the assays described herein, the activity of the polypeptides of the present invention can be measured. Some polymerase polypeptides of the invention exhibit improved polymerase activity as compared to wild type polymerases in the assays described herein.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, Computer Applic. Biol. Sci. 4:11-17 (1988) e.g., as implemented in the program PC/GENE (Intelligenetics, Mountain View, Calif., USA).

The term "substantial identity" of polynucleotide sequences means that a polynucleotide comprises a sequence that has at least 50% sequence identity. Exemplary embodiments include at least: 55%, 60, 65%, 70%, 75%, 80%, 85%, 90%, 94%, 95%, 96%, 97%, 98%, or 99% compared to a reference sequence using the programs described herein; preferably BLAST using standard parameters, as described below. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 65%. Exemplary embodiments include at least 65%, 70%, 75%, 80%, 85%, 90%, 95% 94%, 95%, 96%, 97%, 98% or 99%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Exemplary conservative amino acids substitution groups are: valine-leucine-isoleucine, phenylalanine-tyrosine, lysine-arginine, alanine-valine, aspartic acid-glutamic acid, and asparagine-glutamine.

One of skill in the art will recognize that two polypeptides can also be "substantially identical" if the two polypeptides are immunologically similar. Thus, overall protein structure may be similar while the amino acid sequences of the two polypeptides show significant variation. Therefore, a method to measure whether two polypeptides are substantially identical involves measuring the binding of monoclonal or polyclonal antibodies to each polypeptide. Two polypeptides are substantially identical if the antibodies specific for a first polypeptide bind to a second polypeptide with an affinity of at least one third of the affinity for the first polypeptide. Two polypeptides may also be deemed to be "substantially identical" if they show cross-reactivity in a western blot analysis conducted using methods known in the art.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Accelrys), or by manual alignment and visual inspection.

An example of algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information on the world wide web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, highly stringent conditions are selected to be about 5-10° C. lower than the thermal melting point ($T_m$) for the specific sequence at a defined ionic strength pH. Low stringency conditions are generally selected to be about 15-30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Hybridization conditions are typically those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Exemplary "stringent hybridization conditions" include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'$_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. The "Fc" portion of an antibody refers to that portion of an immunoglobulin heavy chain that comprises one or more heavy chain constant region domains, CH1, CH2 and CH3, but does not include the heavy chain variable region.

The term "osmolyte" as used herein refers to any substance or compound that affects osmosis and/or contributes to the regulation of osmotic pressure in tissues and cells.

Overview

The present invention provides methods and compositions for improving the efficiency and specificity of nucleic acid amplification reactions.

In one aspect, the present invention provides a hybrid polymerase comprising a polymerase domain and a DNA binding domain. In one embodiment, hybrid polymerases of the invention comprise mutations that render the polymerases exonuclease deficient. "Exonuclease deficient" as used herein means that the polymerase has a substantially reduced (i.e., less than 10%, 5% or 1% of the 3'-5' exonuclease activity of Pfu DNA polymerase from *Pyrococcus furiosus*) or no exonuclease activity. For example, a double point mutation in the polymerase domain substituting an alanine at positions D141 and E143 can remove or eliminate 3'-5' exonuclease activity. Derbyshire et al., *Methods in Enzymology*, Vol 262 (1995), pages 363-385. Hybrid polymerases comprising such double point mutations will generally show an increased specificity in nucleic acid amplification reactions, resulting in fewer amplification byproducts (such as amplification of primer-dimers) and increased efficiency in amplification of the desired target nucleic acids.

In a further embodiment, the DNA binding domain of hybrid polymerases of the invention comprises the Sso7d protein. Conjugation of polymerase domains to DNA binding domains such as Sso7d increases the processivity of the polymerases, resulting in an increased amount of amplification product.

In a further aspect, the invention provides methods, compositions, reaction mixtures, and kits for performing nucleic acid amplification reactions that use hybrid polymerases complexed with hot-start antibodies. Such hot-start antibodies bind to the hybrid polymerases in such a way as to inhibit polymerase activity at lower (ambient) temperatures. For example, in some embodiments, the antibodies substantially inhibit the polymerase activity at 50° C., 60° C., and even 72° C., so that substantially no DNA synthesis occurs during the reaction setup at room temperature as well as during the initial heating up of the thermal cycler block from room temperature to, e.g., 95° C. These antibodies will disassociate from the polymerases at higher temperatures, thus releasing the inhibition of the polymerase activity. Such antibodies increase the efficiency of nucleic acid amplification reactions, because the polymerase remains inactive during initial set-up of the amplification reaction and prior to the initial denaturation step. Since it is inactive at low temperatures, the polymerase complexed with the antibody cannot elongate non-specific primer-template hybrids that may form at the lower temperatures.

In a still further aspect, the invention provides methods, compositions, reaction mixtures and kits for performing nucleic acid amplification reactions in the presence of additives that serve to improve the efficiency and specificity of such reactions. In one embodiment, the nucleic acid amplification reaction is conducted in the presence of an osmolyte, such as sarcosine. Sarcosine is known to stabilize proteins in aqueous solutions. Conventional methods of using sarcosine utilize concentrations in the molar range, but in the present invention, concentrations in the millimolar range, generally 50 millimolar or lower, resulted in improved efficiency of the amplification reaction. In a further embodiment, molecules that mimic the electrostatic property of double-stranded DNA are included in the reaction mixture to reduce non-specific binding of the polymerase to double-stranded template nucleic acids. In a still further embodiment, the molecules included to reduce such non-specific binding are heparin molecules.

Hybrid Polymerases Useful in the Present Invention

The present invention provides hybrid polymerases comprising a polymerase domain and a DNA binding domain. Such hybrid polymerases are known to show an increased processivity. See e.g., U.S. Patent Application Publication Nos. 2006/005174; 2004/0219558; 2004/0214194; 2004/0191825; 2004/0081963; 2004/0002076; 2003/0162173; 2003/0148330; 2003/0138830 and U.S. Pat. Nos. 6,627,424 and 7,445,898, each of which is hereby incorporated by reference in its entirety for all purposes and in particular for all teachings related to polymerases, hybrid/chimeric polymerases, as well as all methods for making and using such polymerases.

In one aspect, the present invention provides hybrid polymerases that lack 3'-5' exonuclease activity. In one embodiment, such hybrid polymerases comprise a double point mutation in the polymerase domain that provides this exonuclease deficiency. A variety of mutations can be introduced into a native polymerase domain to reduce or eliminate 3'-5' exonuclease activity. For example, U.S. Pat. Nos. 6,015,668; 5,939,301 and 5,948,614 describe mutations of a metal-binding aspartate to an alanine residue in the 3'-5' exonuclease domain of the Tma and Tne DNA polymerases. These mutations reduce the 3'-5' exonuclease activities of these enzymes to below detectable levels. Similarly, U.S. Pat. No. 5,882,904 describes an analogous aspartate-to-alanine mutation in *Thermococcus barossi*, and U.S. Pat. No. 5,489,523 teaches the double-mutant D141A E143A of the *Pyrococcus wosei* DNA polymerases. Both of these mutant polymerases have virtually no detectable 3'-5' exonuclease activity. Methods of assaying 3'-5' exonuclease activity are well-known in the art. See, e.g., Freemont et al., *Proteins* 1:66 (1986); Derbyshire et al., *EMBO J.* 16:17 (1991) and Derbyshire et al., *Methods in Enzymology* 262: 363 85 (1995). It will be understood that while the above-described mutations were originally identified in one polymerase, one can generally introduce such mutations into other polymerases to reduce or eliminate exonuclease activity. In a specific embodiment, a polymerases of the invention comprise the double point mutation D141A/E143A in the polymerase domain. The phrase "corresponding to a position," in reference to polymerase amino acids, refers to an amino acid that aligns with the same amino acid (e.g., D141 or E143) in a reference polymerase amino acid sequence (e.g., SEQ ID NO:2). Sequence comparisons can be performed using any BLAST including BLAST 2.2 algorithm with default parameters, described in Altschul et al., *Nuc. Acids Res.* 25:3389 3402 (1977) and Altschul et al., *J. Mol. Biol.* 215:403 410 (1990), respectively.

In a further embodiment, hybrid polymerases of the invention are encoded by a nucleotide sequence according to SEQ ID NO: 1. In a still further embodiment, hybrid polymerases of the invention are encoded by a nucleotide sequence that has about 50%, 55%, 60%, 65%, 70%, 75%, 80%, 85%, 90%, 91%, 92%, 93%, 94%, 95%, 96%, 97%, 98%, and 99% sequence identity to SEQ ID NO:1.

In a further embodiment, hybrid polymerases of the invention have an amino acid sequence according to SEQ ID NO: 2. In a still further embodiment, hybrid polymerases of the invention have an amino acid sequence with about 50%, 55%, 60%, 65%, 70%, 75%, 80%, 85%, 90%, 91%, 92%, 93%, 94%, 95%, 96%, 97%, 98%, and 99% sequence identity to SEQ ID NO: 2.

In some embodiments, the binding domain of hybrid polymerases of the invention are from a thermostable organism and provides enhanced activity at higher temperatures, e.g., temperatures above 45° C. For example, Sso7d and Sac7d are small (about 7 kd MW), basic chromosomal proteins from the hyperthermophilic archaeabacteria *Sulfolobus solfataricus* and *S. acidocaldarius*, respectively (see, e.g., Choli et al., *Biochimica et Biophysica Acta* 950:193-203, 1988; Baumann et al., *Structural Biol.* 1:808-819, 1994; and Gao et al, *Nature Struc. Biol.* 5:782-786, 1998). These proteins bind DNA in a sequence-independent manner and when bound, increase the $T_m$ of DNA by up to 40° C. under some conditions (McAfee et al., Biochemistry 34:10063-10077, 1995). These proteins and their homologs are often used as the sequence-non-specific DNA binding domain in improved polymerase fusion proteins. Sso7d, Sac7d, Sac7e and related sequences (referred to herein as "Sso7 sequences" or "Sso7 domains") are known in the art (see, e.g., accession numbers (P39476 (Sso7d); P13123 (Sac7d); and P13125 (Sac7e)). These sequences typically have at least 75% or greater, of 80%, 85%, 90%, or 95% or greater, amino acid sequence identity. For example, an Sso7 protein typically has at least 75% identity to an Sso7d sequence.

In further embodiments, hybrid polymerases of use in the present invention are described for example in U.S. Patent Application Publication Nos. 2006/005174; 2004/0219558; 2004/0214194; 2004/0191825; 2004/0081963; 2004/0002076; 2003/0162173; 2003/0148330; 2003/0138830 and U.S. Pat. Nos. 6,627,424 and 7,445,898, each of which is hereby incorporated by reference in its entirety for all purposes and in particular for all teachings related to polymerases, hybrid/chimeric polymerases, as well as all methods for making and using such polymerases. Examples of hybrid polymerase proteins and methods of generating hybrid proteins are also disclosed in WO2004011605, which is hereby incorporated by reference in its entirety for all purposes, and in particular for all teachings related to generating hybrid proteins.

One advantage of some of the polymerases of the invention is their ability to amplify target nucleic acids in the presence of a substance at concentrations of the substance that typically inhibits PCR amplifications using wildtype Taq polymerase. Examples of such inhibitory substances include, but are not limited to, blood, intact cells, and food samples. Accordingly, the polymerases of the invention can be used to amplify nucleic acids in whole blood or serum, optionally where the blood or serum are not purified before addition to the reaction mixture. In some embodiments, the polymerases of the invention are used to amplify whole cells, including but not limited to whole bacterial, fungal, or yeast cells, e.g., in whole colony PCR. In some embodiments, the polymerases of the invention are used to amplify a nucleic acid in a food sample, optionally without further purification or with partial purification of the nucleic acid from the food sample prior to amplification. This is useful, for example, for screening for bacterial, fungal, or viral contamination of foodstuffs. Exemplary food samples include, but are not limited to, samples comprising coco, cheese, meat, egg, etc.

In some embodiments, the polymerases of the invention are capable of particularly rapid amplification due to its improved processivity. For example, in some embodiments the polymerases of the invention are used in an amplification reaction having an extension time of less than 5, 4, 3, 2, or 1 second, and yet amplifying the target nucleic acid, e.g., with high efficiency (e.g., greater than 90%, 95% or more).

Polymerase Domains

In one exemplary embodiment, hybrid polymerases of the invention have a polymerase domain derived from two parental polymerases, Pfu and DeepVent. Such polymerases are described for example in U.S. Application Publication Nos. 20040219558; 20040214194; 20040191825; 20030162173, each of which is hereby incorporated by reference in its entirety for all purposes and in particular for all teachings related to hybrid polymerases.

A variety of polymerases can be used as at least a portion of the polymerase domain of hybrid polymerases of the invention. At least five families of DNA-dependent DNA polymerases are known, although most fall into families A, B and C. There is little or no structural or sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, δ, and ε are implicated in nuclear replication, and a family A polymerase, polymerase γ, is used for mitochondrial DNA replication. Other types of DNA polymerases include phage polymerases. Any of these polymerases, combinations of all or portions of these polymerases, as well as chimeras or hybrids between two or more of such polymerases or their equivalents can be used to form a portion or all of the polymerase domain of hybrid polymerases of the invention.

Further, in some embodiments, non-thermostable polymerases may also be used in accordance with the invention. For example, the large fragment of *E. coli* DNA Polymerase I (Klenow) (the Klenow Fragment) with mutation (D355A, E357A) abolishes the 3'=>5' exonuclease activity. This enzyme or equivalent enzymes can be used in embodiments where the amplification reaction is not performed at high temperatures.

In some embodiments, the hybrid polymerases of the invention include a polymerase domain comprising mutations that reduce or abolish exonuclease activity of any hybrid polymerase comprising such a polymerase domain in comparison to a hybrid polymerase comprising a polymerase domain that does not have such mutations. In further embodiments, such hybrid polymerases comprise mutations in the exonuclease domain. In still further embodiments, such hybrid polymerases comprise an amino acid sequence according to SEQ ID NO: 2.

Nucleic Acid Binding Domains

In some embodiments, hybrid polymerases of the invention comprise a polymerase domain conjugated to a DNA binding domain. A DNA binding domain is a protein, or a defined region of a protein, that binds to nucleic acid in a sequence-independent matter, e.g., binding does not exhibit a gross preference for a particular sequence. DNA binding domains may bind single or double stranded nucleic acids.

The DNA binding proteins of use in the invention are generally thermostable. Examples of such proteins include, but are not limited to, the Archaeal small basic DNA binding proteins Sso7d and Sso7d-like proteins (see, e.g., Choli et al., Biochimica et Biophysica Acta 950:193-203, 1988; Baumann et al., Structural Biol. 1:808-819, 1994; and Gao et al, Nature Struc. Biol. 5:782-786, 1998), Archaeal HMf-like proteins (see, e.g., Starich et al., J. Molec. Biol. 255: 187-203, 1996; Sandman et al., Gene 150:207-208, 1994), and PCNA homologs (see, e.g., Cann et al., J. Bacteriology 181:6591-6599, 1999; Shamoo and Steitz, Ce11:99, 155-166, 1999; De Felice et al., J. Molec. Biol. 291, 47-57, 1999; and Zhang et al., Biochemistry 34:10703-10712, 1995).

Sso7d and Sso7d-like proteins, Sac7d and Sac7d-like proteins, e.g., Sac7a, Sac7b, Sac7d, and Sac7e are small (about 7,000 kd MW), basic chromosomal proteins from the hyperthermophilic archaebacteria *Sulfolobus solfataricus* and *S. acidocaldarius*, respectively. These proteins are lysine-rich and have high thermal, acid and chemical stability. They bind DNA in a sequence-independent manner and when bound, increase the $T_m$ of DNA by up to 40° C. under some conditions (McAfee, Biochemistry 34:10063-10077, 1995; Gao et al., Nat. Struct. Biol. 5(9):782-786, 1998). These proteins and their homologs are typically believed to be involved in stabilizing genomic DNA at elevated temperatures. Suitable Sso7d-like DNA binding domains for use in the invention can be modified based on their sequence homology to Sso7d. Typically, DNA binding domains that are identical to or substantially identical to a known DNA binding protein over a comparison window of about 25 amino acids, optionally about 50-100 amino acids, or the length of the entire protein, can be used in the invention. The sequence can be compared and aligned for maximum correspondence over a comparison window, or designated region as measured using one of the described comparison algorithms or by manual alignment and visual inspection. In some embodiments, the DNA polymerase comprises SEQ ID NO: 3 or a substantially (e.g., at least 60%, 70%, 80%, 90%, 95%) identical sequence thereof. A variety of mutations in the Sso7 binding domain have been described in, e.g., US Patent Application Nos. 2005/0048530 and 2007/0141591.

The HMf-like proteins are archaeal histones that share homology both in amino acid sequences and in structure with eukaryotic H4 histones, which are thought to interact directly with DNA. The HMf family of proteins form stable dimers in solution, and several HMf homologs have been identified from thermostable species (e.g., *Methanothermus fervidus* and *Pyrococcus* strain GB-3a). The HMf family of proteins, once joined to Taq DNA polymerase or any DNA modifying enzyme with a low intrinsic processivity, can enhance the ability of the enzyme to slide along the DNA substrate and thus increase its processivity. For example, the dimeric HMf-like protein can be covalently linked to the N terminus of Taq DNA polymerase, e.g., via chemical modification, and thus improve the processivity of the polymerase.

Certain helix-hairpin-helix motifs have been shown to bind DNA nonspecifically and enhance the processivity of a DNA polymerase to which it is fused (Pavlov et al., Proc Natl Acad Sci USA. 99:13510-5, 2002).

Additional DNA binding domains suitable for use in the invention can be identified by homology with known DNA binding proteins and/or by antibody crossreactivity, or may be found by means of a biochemical assay. DNA binding domains may be synthesized or isolated using the techniques described herein and known in the art.

Sequence non-specific doubled-stranded nucleic acid binding domains for use in the invention can also be identified by cross-reactivity using antibodies, including but not limited to polyclonal antibodies, that bind to known nucleic acid binding domains. Polyclonal antibodies are generated using methods well known to those of ordinary skill in the art (see, e.g., Coligan, Current Protocols in Immunology (1991); Harlow & Lane, Antibodies, A Laboratory Manual (1988)). Those proteins that are immunologically cross-reactive binding proteins can then be detected by a variety of assay methods. For descriptions of various formats and conditions that can be used, see, e.g., Methods in Cell Biology: Antibodies in Cell Biology, volume 37 (Asai, ed. 1993), Coligan, supra, and Harlow & Lane, supra.

Specificity for binding to double-stranded nucleic acids can be tested using a variety of assays known to those of ordinary skill in the art. These include such assays as filter binding assays or gel-shift assays. For example, in a filter-binding assay the polypeptide to be assessed for binding activity to double-stranded DNA is pre-mixed with radio-labeled DNA, either double-stranded or single-stranded, in the appropriate buffer. The mixture is filtered through a membrane (e.g., nitrocellulose) which retains the protein and the protein-DNA complex. The amount of DNA that is retained on the filter is indicative of the quantity that bound to the protein. Binding can be quantified by a competition analysis in which binding of labeled DNA is competed by the addition of increasing amounts of unlabelled DNA. A polypeptide that binds double-stranded DNA at a 10-fold or greater affinity than single-stranded DNA is defined herein as a double-stranded DNA binding protein. Alternatively, binding activity can be assessed by a gel shift assay in which radiolabeled DNA is incubated with the test polypeptide. The protein-DNA complex will migrate slower through the gel than unbound DNA, resulting in a shifted band. The amount of binding is assessed by incubating samples with increasing amounts of double-stranded or single-stranded unlabeled DNA, and quantifying the amount of radioactivity in the shifted band.

A binding domain suitable for use in the invention binds to double-stranded nucleic acids in a sequence-independent fashion, i.e., a binding domain of the invention binds double-stranded nucleic acids with a significant affinity, but, there is no known nucleic acid that binds to the domain with more than 100-fold more affinity than another nucleic acid with the same nucleotide composition, but a different nucleic acid sequence. Non-specific binding can be assayed using methodology similar to that described for determining double-stranded vs. single-stranded nucleic acid binding. Filter binding assays or gel mobility shift assays can be performed as above using competitor DNAs of the same nucleotide composition, but different nucleic acid sequences to determine specificity of binding.

Sequence non-specific double-stranded nucleic acid binding domains for use in the invention can also be assessed, for example, by assaying the ability of the double-stranded binding domain to increase processivity or efficiency of a modifying enzyme or to increase the stability of a nucleic acid duplex by at least 1° C. can be determined.

A binding domain of the invention can also be identified by direct assessment of the ability of such a domain to stabilize a double-stranded nucleic acid conformation. For example, a melting curve of a primer-template construct can be obtained in the presence or absence of protein by monitoring the UV absorbance of the DNA at 260 nm. The $T_m$ of the double-stranded substrate can be determined from the midpoint of the melting curve. The effect of the sequence-non-specific double-stranded nucleic-acid-binding protein on the $T_m$ can then be determined by comparing the $T_m$ obtained in the presence of the modified enzyme with that in the presence of the unmodified enzyme. (The protein does not significantly contribute to the UV absorbance because it has a much lower extinction coefficient at 260 nm than DNA). A domain that increases the $T_m$ by 1° C., often by 5° C., 10° C. or more, can then be selected for use in the invention.

Novel sequence non-specific double-stranded nucleic acid binding proteins of the invention can also be isolated by taking advantage of their DNA binding activity, for instance by purification on DNA-cellulose columns. The isolated proteins can then be further purified by conventional means, sequenced, and the genes cloned by conventional means via PCR. Proteins overexpressed from these clones can then be tested by any of the means described above.

Producing Polymerases of the Invention polymerases of the invention are generally produced by joining a polymerase domain to a DNA binding domain using chemical and/or recombinant methods.

polymerases of the invention can be produced using techniques known in the art. Methods for producing polymerases comprising a polymerase domain and a nucleic acid binding domain are described, for example, in U.S. Patent Application Publication Nos. 2006/005174; 2004/0219558; 2004/0214194; 2004/0191825; 2004/0081963; 2004/0002076; 2003/0162173; 2003/0148330; 2003/0138830 and U.S. Pat. Nos. 6,627,424 and 7,445,898, each of which is hereby incorporated by reference in its entirety for all purposes and in particular for all teachings related to polymerases, hybrid/chimeric polymerases, as well as all methods for making and using such polymerases.

Chemical methods of joining a DNA binding protein to a polymerase domain are described, e.g., in Bioconjugate Techniques, Hermanson, Ed., Academic Press (1996). These include, for example, derivatization for the purpose of linking the two proteins to each other, either directly or through a linking compound, by methods that are well known in the art of protein chemistry. For example, in one chemical conjugation embodiment, the means of linking the catalytic domain and the DNA binding domain comprises a heterobifunctional-coupling reagent which ultimately contributes to formation of an intermolecular disulfide bond between the two moieties. Other types of coupling reagents that are useful in this capacity for the present invention are described, for example, in U.S. Pat. No. 4,545,985. Alternatively, an intermolecular disulfide may conveniently be formed between cysteines in each moiety, which occur naturally or are inserted by genetic engineering. The means of linking moieties may also use thioether linkages between heterobifunctional crosslinking reagents or specific low pH cleavable crosslinkers or specific protease cleavable linkers or other cleavable or noncleavable chemical linkages.

The methods of linking a DNA binding domain, e.g., Sso7d, and a polymerase domain may also comprise a peptidyl bond formed between moieties that are separately synthesized by standard peptide synthesis chemistry or recombinant means. The conjugate protein itself can also be produced using chemical methods to synthesize an amino acid sequence in whole or in part. For example, peptides can be synthesized by solid phase techniques, such as, e.g., the Merrifield solid phase synthesis method, in which amino acids are sequentially added to a growing chain of amino acids (see, Merrifield (1963) J. Am. Chem. Soc., 85:2149-2146). Equipment for automated synthesis of polypeptides is commercially available from suppliers such as PE Corp. (Foster City, Calif.), and may generally be operated according to the manufacturer's instructions. The synthesized peptides can then be cleaved from the resin, and purified, e.g., by preparative high performance liquid chromatography (see Creighton, Proteins Structures and Molecular Principles, 50-60 (1983)). The composition of the synthetic polypeptides or of subfragments of the polypeptide, may be confirmed by amino acid analysis or sequencing (e.g., the Edman degradation procedure; see Creighton, Proteins, Structures and Molecular Principles, pp. 34-49 (1983)).

In another embodiment, a DNA binding domain and polymerase domain can be joined via a linking group. The linking group can be a chemical crosslinking agent, including, for example, succinimidyl-(N-maleimidometh-yl)-cyclohexane-1-carboxylate (SMCC). The linking group can also be an additional amino acid sequence(s), including, for example, a polyalanine, polyglycine or similarly, linking group.

In some embodiments, the coding sequences of each polypeptide in a resulting fusion protein (also referred to herein as "hybrid" and/or "chimeric" or "chimera" protein) are directly joined at their amino- or carboxy-terminus via a peptide bond in any order. Alternatively, an amino acid linker sequence may be employed to separate the first and second polypeptide components by a distance sufficient to ensure that each polypeptide folds into its secondary and tertiary structures. Such an amino acid linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Typical peptide linker sequences contain Gly, Ser, Val and Thr residues. Other near neutral amino acids, such as Ala can also be used in the linker sequence. Amino acid sequences which may be usefully employed as linkers include those disclosed in Maratea et al. (1985) Gene 40:39-46; Murphy et al. (1986) Proc. Natl. Acad. Sci. USA 83:8258-8262; U.S. Pat. Nos. 4,935,233 and 4,751,180, each of which is hereby incorporated by reference in its entirety for all purposes and in particular for all teachings related to linkers. The linker sequence may generally be from 1 to about 50 amino acids in length, e.g., 3, 4, 6, or 10 amino acids in length, but can be 100 or 200 amino acids in length. Linker sequences may not be required when the first and second polypeptides have non-essential N-terminal amino acid regions that can be used to separate the functional domains and prevent steric interference. In some embodiments, linker sequences of use in the present invention comprise an amino acid sequence according to SEQ ID NO: 5.

Other chemical linkers include carbohydrate linkers, lipid linkers, fatty acid linkers, polyether linkers, e.g., PEG, etc. For example, poly(ethylene glycol) linkers are available from Shearwater Polymers, Inc. Huntsville, Ala. These linkers optionally have amide linkages, sulfhydryl linkages, or heterobifunctional linkages.

Other methods of joining a DNA binding domain and polymerase domain include ionic binding by expressing negative and positive tails and indirect binding through antibodies and streptavidin-biotin interactions. (See, e.g., Bioconjugate Techniques, supra). The domains may also be joined together through an intermediate interacting sequence. For example, DNA binding domain-interacting sequence, i.e., a sequence that binds to a particular DNA binding domain (such as Sso7d), can be joined to a polymerase. The resulting fusion protein can then be allowed to associate non-covalently with the DNA binding domain to generate a DNA-binding-domain-polymerase conjugate.

As previously described, nucleic acids encoding the polymerase or DNA binding domains can be obtained using routine techniques in the field of recombinant genetics. Basic texts disclosing the general methods of use in this invention include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-1999). Such nucleic acids may also be obtained through in vitro amplification methods such as those described herein and in Berger, Sambrook, and Ausubel, as well as Mullis et al., (1987) U.S. Pat. No. 4,683,202; PCR Protocols A Guide to Methods and Applications (Innis et al., eds) Academic Press Inc. San Diego, Calif. (1990) (Innis); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Natl. Acad. Sci. USA 87, 1874; Lomell et al. (1989) J. Clin. Chem., 35: 1826; Landegren et al., (1988) Science 241: 1077-1080; Van Brunt (1990) Biotechnology 8: 291-294; Wu and Wallace (1989) Gene 4: 560; and Barringer et al. (1990) Gene 89: 117, each of which is incorporated by reference in its entirety for all purposes and in particular for all teachings related to amplification methods.

One of skill will recognize that modifications can additionally be made to the polymerases of the present invention without diminishing their biological activity. Some modifications may be made to facilitate the cloning, expression, or incorporation of a domain into a fusion protein. Such modifications are well known to those of skill in the art and include, for example, the addition of codons at either terminus of the polynucleotide that encodes the binding domain to provide, for example, a methionine added at the amino terminus to provide an initiation site, or additional amino acids (e.g., poly His) placed on either terminus to create conveniently located restriction sites or termination codons or purification sequences.

The polymerases of the present invention can be expressed in a variety of host cells, including E. coli, other bacterial hosts, yeasts, filamentous fungi, and various higher eukaryotic cells such as the COS, CHO and HeLa cells lines and myeloma cell lines. Techniques for gene expression in microorganisms are described in, for example, Smith, Gene Expression in Recombinant Microorganisms (Bioprocess Technology, Vol. 22), Marcel Dekker, 1994. Examples of bacteria that are useful for expression include, but are not limited to, Escherichia, Enterobacter, Azotobacter, Erwinia, Bacillus, Pseudomonas, Klebsielia, Proteus, Salmonella, Serratia, Shigella, Rhizobia, Vitreoscilla, and Paracoccus. Filamentous fungi that are useful as expression hosts include, for example, the following genera: Aspergillus, Trichoderma, Neurospora, Penicillium, Cephalosporium, Achlya, Podospora, Mucor, Cochliobolus, and Pyricularia. See, e.g., U.S. Pat. No. 5,679,543 and Stahl and Tudzynski, Eds., Molecular Biology in Filamentous Fungi, John Wiley & Sons, 1992. Synthesis of heterologous proteins in yeast is well known and described in the literature. Methods in Yeast Genetics, Sherman, F., et al., Cold Spring Harbor Laboratory, (1982) is a well recognized work describing the various methods available to produce the enzymes in yeast.

There are many expression systems for producing the polymerase polypeptides of the present invention that are well known to those of ordinary skill in the art. (See, e.g., Gene Expression Systems, Fernandex and Hoeffler, Eds. Academic Press, 1999; Sambrook and Russell, supra; and Ausubel et al, supra.) Typically, the polynucleotide that encodes the variant polypeptide is placed under the control of a promoter that is functional in the desired host cell. Many different promoters are available and known to one of skill in the art, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the nucleic acids that encode the joined polypeptides are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., Nature (1977) 198: 1056), the tryptophan (trp) promoter system (Goeddel et al., Nucleic Acids Res. (1980) 8: 4057), the tac promoter (DeBoer, et al., Proc. Natl. Acad. Sci. U.S.A. (1983) 80:21-25); and the lambda-derived PL promoter and N-gene ribosome binding site (Shimatake et al., Nature (1981) 292: 128). The particular promoter system is not critical to the invention, any available promoter that functions in prokaryotes can be used. Standard bacterial expression vectors include plasmids such as pBR322-based plasmids, e.g., pBLUESCRIPT™, pSKF, pET23D, lambda-phage derived vectors, and fusion expression systems such as GST and LacZ. Epitope tags can also be added to recombinant proteins to provide convenient methods of isolation, e.g., c-myc, HA-tag, 6-His tag (SEQ ID NO:46), maltose binding protein, VSV-G tag, anti-DYKDDDDK tag (SEQ ID NO:47), or any such tag, a large number of which are well known to those of skill in the art.

For expression in prokaryotic cells other than E. coli, a promoter that functions in the particular prokaryotic species is required. Such promoters can be obtained from genes that have been cloned from the species, or heterologous promoters can be used. For example, the hybrid trp-lac promoter functions in Bacillus sp. in addition to E. coli. These and other suitable bacterial promoters are well known in the art and are described, e.g., in Sambrook et al. and Ausubel et al. Bacterial expression systems for expressing the proteins of the invention are available in, e.g., E. coli, Bacillus sp., and Salmonella (Palva et al., Gene 22:229-235 (1983); Mosbach et al., Nature 302:543-545 (1983). Kits for such expression systems are commercially available.

Eukaryotic expression systems for mammalian cells, yeast, and insect cells are well known in the art and are also commercially available. In yeast, vectors include Yeast Integrating plasmids (e.g., YIp5) and Yeast Replicating plasmids (the YRp series plasmids) and pGPD-2. Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Either constitutive or regulated promoters can be used in the present invention. Regulated promoters can be advantageous because the host cells can be grown to high densities before expression of the fusion polypeptides is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals.

For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) Gene 25: 167; de Boer et al. (1983) Proc. Nat'l. Acad. Sci. USA 80: 21), and the bacteriophage T7 promoter (Studier et al. (1986) J. Mol. Biol.; Tabor et al. (1985) Proc. Nat'l Acad. Sci. USA 82: 1074-8). These promoters and their use are also discussed in Sambrook et al., supra.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), J. Biol. Chem. 263: 16297-16302.

The construction of polynucleotide constructs generally requires the use of vectors able to replicate in bacteria. Such vectors are commonly used in the art. A plethora of kits are commercially available for the purification of plasmids from bacteria (for example, EasyPrep™, FlexiPrep™, from Pharmacia Biotech; StrataClean™, from Stratagene; and, QIAexpress® Expression System, Qiagen). The isolated and purified plasmids can then be further manipulated to produce other plasmids, and used to transform cells.

The polypeptides of the present invention can be expressed intracellularly, or can be secreted from the cell. Intracellular expression often results in high yields. If necessary, the amount of soluble, active fusion polypeptide may be increased by performing refolding procedures (see, e.g., Sambrook et al., supra.; Marston et al., Bio/Technology (1984) 2: 800; Schoner et al., Bio/Technology (1985) 3: 151). Polypeptides of the invention can be expressed in a variety of host cells, including *E. coli*, other bacterial hosts, yeast, and various higher eukaryotic cells such as the COS, CHO and HeLa cells lines and myeloma cell lines. The host cells can be mammalian cells, insect cells, or microorganisms, such as, for example, yeast cells, bacterial cells, or fungal cells.

Once expressed, the polypeptides can be purified according to standard procedures of the art, including ammonium sulfate precipitation, affinity columns, column chromatography, gel electrophoresis and the like (see, generally, R. Scopes, Protein Purification, Springer-Verlag, N.Y. (1982), Deutscher, Methods in Enzymology Vol. 182: Guide to Protein Purification, Academic Press, Inc. N.Y. (1990)). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production).

To facilitate purification of the polypeptides of the invention, the nucleic acids that encode the polypeptides can also include a coding sequence for an epitope or "tag" for which an affinity binding reagent is available. Examples of suitable epitopes include the myc and V-5 reporter genes; expression vectors useful for recombinant production of fusion polypeptides having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to the fusion proteins of the invention, and corresponding detection systems are known to those of skill in the art, and several are commercially available (e.g., FLAG" (Kodak, Rochester N.Y.). Another example of a suitable tag is a polyhistidine sequence, which is capable of binding to metal chelate affinity ligands. Typically, six adjacent histidines (SEQ ID NO:46) are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, N.Y.; commercially available from Qiagen (Santa Clarita, Calif.)).

One of skill in the art would recognize that after biological expression or purification, the polymerase peptide(s) may possess a conformation substantially different than the native conformations of the constituent polypeptides. In this case, it may be necessary or desirable to denature and reduce the polypeptide and then to cause the polypeptide to re-fold into the preferred conformation. Methods of reducing and denaturing proteins and inducing re-folding are well known to those of skill in the art (See, Debinski et al. (1993) J. Biol. Chem. 268: 14065-14070; Kreitman and Pastan (1993) Bioconjug. Chem. 4: 581-585; and Buchner et al. (1992) Anal. Biochem. 205: 263-270). Debinski et al., for example, describe the denaturation and reduction of inclusion body proteins in guanidine-DTE. The protein is then refolded in a redox buffer containing oxidized glutathione and L-arginine.

Hot-Start Methods

In some embodiments, hybrid polymerases of the invention are used in nucleic acid amplification methods, particularly quantitative PCR (qPCR) methods. In such amplification methods, it can be beneficial to employ "hot start" methods to decrease the generation of primer dimers and unspecific amplification products at ambient temperatures. A number of hot-start methods are known. These include physical separation of the polymerase, use of nucleic acid additives to inhibit extension reactions at low temperatures, and modifications to the active site of the polymerase. Often, it may be desirable to use "hot start" polymerases. In a hot-start polymerase, a molecule is typically bound to the enzyme at the active site to inhibit polymerase activity at lower temperatures. The molecule is removed at high temperatures (e.g., at 95° C.) to allow the polymerase to function at the desired point of the process. The molecule can be one or more antibody, peptide, or a small organic molecule. For example, hot-start can be achieved using one or more antibody that binds to a polymerase with high affinity at ambient temperatures in an inhibitory manner. The complex is dissociated in a high temperature preheating step.

A polymerase may also be chemically modified for hot-start. Heat labile blocking groups are introduced into the polymerase, which render the enzyme inactive at room temperature. These blocking groups are removed at high temperature prior to cycling such that the enzyme is activated. Heat labile modifications include coupling citraconic anhydride or aconitric anhydride to lysine residues of the enzyme are known in the art, see e.g., U.S. Pat. No. 5,677,152, which is hereby incorporated by reference in its entirety for all purposes and in particular for all teachings related to hot-start methods.

U.S. Patent Application Publication No. 2003/0119150 also discloses a concept of hot start PCR that employs a thermostable exonuclease and a polymerase. This method is based on preventing primer elongation at low temperatures by introducing chemical modifications at the 3' end of at least one primer. A thermostable exonuclease is used that is inactive at ambient temperatures or below. Upon temperature increase, the exonuclease becomes active and capable of removing the 3' modification of the primer to enable it to participate in the amplification reaction. U.S. 20030119150, which is hereby incorporated by reference in its entirety for all purposes and in particular for all teachings related to hot-start methods, further teaches that when hybridization probes are used for real-time monitoring, e.g., TaqMan hybridization probes, Molecular Beacon oligonucleotides, or two oligonucleotide hybridization methods, the presence of a thermostable exonuclease III requires a suitable blocking method for the 3' end of the detection probe to avoid 3' digestion.

Hot-Start Antibodies

In certain embodiments of the invention, monoclonal antibodies are used to provide the hot-start features to hybrid polymerases of the invention.

In one aspect, the present invention provides methods for producing and screening for the appropriate antibodies against hybrid polymerases of the invention, particularly those polymerases that exhibit both 5' to 3' polymerase activity and 3' to 5' exonuclease activity. For such polymerases, it can be beneficial to use one or more antibodies that can sufficiently inhibit either or both the polymerase and the exonuclease activity of the hybrid polymerase. Important features of antibodies of use in this aspect of the invention include binding affinity for the polymerase as well as the ability to block polymerase and/or exonuclease activities.

Hot-start antibodies increase the specificity of amplification reactions, because they render the polymerase inactive at room temperature, thus avoiding extension of nonspecifically annealed primers or primer dimers. The functional activity of the polymerase is restored by disassociating the antibody from the polymerase, generally through incubation at a higher temperature. In some embodiment, such a "higher temperature" is from about 90° to about 99° C. for about 2 to about 10 minutes. It will be appreciated that the temperature and length of time for incubation to disassociate the antibody and activate the polymerase can be varied according to known parameters to provide the most effective method of activating the polymerase in these hot-start methods.

Methods for screening for antibodies of use in the present invention include methods known in the art, such as affinity-based ELISA assays, as well as functional assays for polymerase and/or exonuclease inhibition. For such functional assays, the amount of DNA produced or digested per unit of time can be correlated to the activity of the polymerase or exonuclease used, thus providing an estimate of the amount of inhibition a particular antibody can exert on either or both the polymerase and exonuclease activity of the polymerase.

In one aspect, the present invention provides antibodies that bind to a polymerase including but not limited to a polymerase comprising SEQ ID NO:2. In some embodiments, the antibodies inhibit DNA polymerase activity, and/or, when present 3'-5' exonuclease activity. In some embodiments, the antibodies inhibit DNA polymerase and/or 3'-5' exonuclease activity of a polymerase comprising SEQ ID NO:2 but where position 141 is D and 143 is E in cases where exonuclease activity is measured, but does not significantly inhibit the same polymerase activity of Taq polymerase. In some embodiments, the antibodies inhibit the DNA polymerase and/or exonuclease activity of a DNA polymerase by at least 80% or 90% but does not inhibit DNA polymerase activity of Taq polymerase by more than 15%. Four exemplary antibodies are provided herein as well as sequence information related to their heavy and light variable regions, including all CDR sequences. In some embodiments, the antibodies described herein are complexed with a polymerase.

In some exemplary embodiments, hot-start antibodies of use in the present invention comprise light-chain variable regions with nucleotide sequences of about 75%, 80%, 85%, 90%, 94%, 95%, 96%, 97%, 98%, 99% or 100% sequence identity to any one of SEQ ID NOs: 10-13. Such monoclonal antibodies may in further exemplary embodiments comprise heavy-chain variable regions with nucleotide sequences of about 75%, 80%, 85%, 90%, 94%, 95%, 96%, 97%, 98%, 99% or 100% sequence identity to any one of SEQ ID NOs: 6-9. Such monoclonal antibodies may in still further exemplary embodiments comprise heavy-chain variable regions with amino acid sequences of about 75%, 80%, 85%, 90%, 94%, 95%, 96%, 97%, 98%, 99% or 100% sequence identity to any one of SEQ ID NOs: 14-17 and/or light-chain variable regions with amino acid sequences of about 75%, 80%, 85%, 90%, 94%, 95%, 96%, 97%, 98%, 99% or 100% sequence identity to any one of SEQ ID NOs: 18-21.

In some embodiments, an antibody is provided comprising a heavy chain variable region comprising CDR1, CDR2, and CDR3 as follows: SEQ ID NO:22, SEQ ID NO:23, and SEQ ID NO:24, respectively, and/or a light chain variable region comprising CDR1, CDR2, and CDR3 as follows: SEQ ID NO:25, SEQ ID NO:26, and SEQ ID NO:27, respectively. In some embodiments, the antibody comprises a light chain variable region comprising SEQ ID NO:14 and/or a heavy chain variable region comprising SEQ ID NO:18. In some embodiments, an antibody comprising the CDRs described in this paragraph is used in combination with another of the antibodies described in this application, thereby inhibiting polymerase activity in a DNA polymerase. For example, in some embodiments, an antibody as described above in this paragraph is combined with an antibody comprising a heavy chain variable region comprising CDR1, CDR2, and CDR3 as follows: SEQ ID NO:34, SEQ ID NO:35, and SEQ ID NO:36, respectively, and/or a light chain variable region comprising CDR1, CDR2, and CDR3 as follows: SEQ ID NO:37, SEQ ID NO:38, and SEQ ID NO:39, respectively.

In some embodiments, an antibody is provided comprising a heavy chain variable region comprising CDR1, CDR2, and CDR3 as follows: SEQ ID NO:28, SEQ ID NO:29, and SEQ ID NO:30, respectively, and/or a light chain variable region comprising CDR1, CDR2, and CDR3 as follows: SEQ ID NO:31, SEQ ID NO:32, and SEQ ID NO:33, respectively. In some embodiments, the antibody comprises a light chain variable region comprising SEQ ID NO:15 and/or a heavy chain variable region comprising SEQ ID NO:19. The inventors have found that antibodies comprising the above-described CDRs are particularly effective in inhibiting 3'-5' exonuclease activities in polymerases comprising such activities. In some embodiments, for an antibody comprising the CDRs described in this paragraph is used in combination with another of the antibodies described in this application, thereby inhibiting polymerase and/or 3'-5' exonuclease activities. For example, in some embodiments, an antibody as described above in this paragraph is combined with an antibody comprising a heavy chain variable region comprising CDR1, CDR2, and CDR3 as follows: SEQ ID NO:22, SEQ ID NO:23, and SEQ ID NO:24, respectively, and/or a light chain variable region comprising CDR1, CDR2, and CDR3 as follows: SEQ ID NO:25, SEQ ID NO:26, and SEQ ID NO:27, respectively.

In some embodiments, an antibody is provided comprising a heavy chain variable region comprising CDR1, CDR2, and CDR3 as follows: SEQ ID NO:34, SEQ ID NO:35, and SEQ ID NO:36, respectively, and/or a light chain variable region comprising CDR1, CDR2, and CDR3 as follows: SEQ ID NO:37, SEQ ID NO:38, and SEQ ID NO:39, respectively. In some embodiments, the antibody comprises a heavy chain variable region comprising SEQ ID NO:16 and/or a light chain variable region comprising SEQ ID NO:20. In some embodiments, the antibody comprises a heavy chain variable region comprising SEQ ID NO:17 and/or a light chain variable region comprising SEQ ID NO:21.

The present invention also provides for a polynucleotide encoding a protein (including but not limited to an antibody of antigen fragment thereof) comprising one, two, or three CDRs of any of the heavy or light chains as described above. In some embodiments, the encoded protein comprises a heavy or light variable region, e.g., as set forth in any of SEQ ID NOs:14, 15, 16, 17, 18, 19, 20, or 21. In some embodiments, the protein comprises additional antibody components, and in some cases is a complete antibody heavy or light chain. In some embodiments, the invention provides for expression cassettes or vectors comprising the above-described polynucleotide, as well as host cells (including but not limited to bacterial, fungal, yeast, insect, or mammalian cells) comprising such expression cassettes or vectors.

The antibodies described herein are useful, for example, in "hot start" amplification or other reactions. Accordingly, in some embodiments, they are provided in a kit, optionally also comprising a DNA or RNA polymerase or other reagents for use in nucleic acid amplification.

Additives for Improving Efficiency of Amplification Reactions

In certain aspects, it may be desirable to include an additional compound as an additive to improve efficiency in amplification reactions, including but not limited to qPCR. The amplification reaction comprising the additives can include mixtures comprising polymerases having or lacking 3'-5' exonuclease activity and optionally including a heterologous DNA binding domain. In some embodiments, inclusion of the additive is sufficient to increase efficiency of the polymerase by at least 5, 10, 15, 20, 25, 35, 40, or 50% or more compared to a control mixture lacking the additive.

In some embodiments, a polymerase of the invention exhibits low efficiency for certain targets when used in a formulation that includes certain binding dyes (such as, in one non-limiting example, an EvaGreen DNA binding dye). Such low efficiency may in some embodiments result in a delay of Ct values associated with low input DNA concentrations. Methods for measuring efficiency of a particular reaction are known in the art and described in further detail below.

In some embodiments, the additive is an osmolyte included in an amplification reaction of the invention to improve efficiency. Members of the osmolyte family have been shown to improve the thermal stability of proteins (Santoro, Biochemistry, 1992) as well as decrease DNA double helix stability (Chadalavada, FEBS Letters, 1997). In some embodiments, osmolytes are small molecules or compounds which are produced by living organisms in response to environmental stresses such as extreme temperatures, dehydration, or salinity and which protect their cellular components and help to maintain optimal cytosolic conditions. Osmolytes of use in the present invention may include without limitation sarcosine, trimethylamine N-oxide (TMAO), dimethylsulfoniopropionate, and trimethylglycine. Sarcosine is chemically similar to betaine, a chemical which has been shown to improve conventional PCR (Henke, Nucleic Acids Research, 1997).

In conventional uses of osmolytes, the stabilizing effects of such compounds are generally observed at relatively high concentrations (>1M). However, in methods of the present invention, millimolar concentrations of osmolytes have been found to be effective for improving the reaction efficiency of amplification reactions such as qPCR. Without being bound by a mechanism of action, it is possible that the improvement in efficiency is the result of improving the accessibility of the DNA polymerase to the targeted region of the DNA template for reactions that contain low concentrations of input DNA sample. In some embodiments, concentrations of about 100 to about 1000 mM of osmolytes are used in methods and kits of the present invention. In still further embodiments, concentrations of about 50 to about 700, about 100 to about 600, about 150 to about 500, about 200 to about 400 mM, and about 300 to about 350 mM osmolytes are used in methods and kits of the invention. In some embodiments, the osmolyte used in methods, reaction mixtures, and kits of the invention is sarcosine (optionally at the above-listed concentrations). As shown in FIG. 1, addition of sarcosine improved the efficiency of the amplification reaction as compared to control lacking sarcosine.

In some embodiments, particularly in the amplification of low-copy target nucleic acids, efficiency decreases due to the binding of polymerase to non-primed double-stranded nucleic acid targets. Binding of the polymerase to the double-stranded targets will prevent those targets from denaturation, hybridizing to primers, and undergoing an amplification reaction. To improve the specificity of the polymerase for primed templates, in some embodiments methods of the invention utilize heparin. Heparin molecules, which are negatively charged, can be included in the reaction mixture to mimic the electrostatic property of double stranded nucleic acids. The addition of heparin can, without being limited to a mechanism of action, prevent excess polymerase from binding to the double-stranded template until a single-stranded primed-template becomes available. In some exemplary embodiments, heparin is used in methods and kits of the invention at concentrations of about 50 to about 750 pg/µl. In further exemplary embodiments, heparin is used in methods and kits of the invention at concentrations of about 75 to about 700, about 100 to about 600, about 125 to about 500, about 150 to about 400, about 175 to about 300, and about 200 to about 250 pg/µl. Other molecules known in the art can be used in a similar manner to prevent non-specific binding of the polymerase to non-primed double-stranded template.

Amplification Reactions Utilizing Compositions of the Invention

As discussed herein, the present invention provides different compositions, including hybrid polymerases, hot-start antibodies and reaction additives, for use in nucleic acid amplification reactions. Such amplification reactions include without limitation polymerase chain reaction (PCR), DNA ligase chain reaction (LCR), QBeta RNA replicase, and RNA transcription-based (such as TAS and 3SR) amplification reactions as well as others known to those of skill in the art. Polymerase chain reactions that can be conducted using the compositions described herein include without limitation reverse-transcription PCR (rt-PCR) and quantitative PCR (qPCR).

As will be appreciated, any combination of the different components described herein is encompassed by the present invention, as are amplification reactions utilizing any combination of different components of the invention. For example, amplification reactions of the invention may utilize hybrid polymerases comprising one or mutations that remove or completely abolish exonuclease activity, particularly 3'-5' exonuclease activity. Such amplification reactions may further utilize such mutant hybrid polymerases combined with hot-start antibodies. Some amplification reactions of the invention may utilize mutant hybrid polymerases comprising the D141A/E143A double point mutation combined with additives such as sarcosine or heparin. Some amplification reactions of the invention may also utilize mutant hybrid polymerases lacking 3'-5' exonuclease activity combined with hot-start antibodies and with additives such as sarcosine or heparin. Further combinations are easily identified by one of skill in the art using the disclosure provided herein.

Amplification reactions, such as polymerase chain reaction (PCR) methods, show an improved efficiency and specificity when compositions of the invention are components of such reactions. Typically, "efficiency" as discussed herein is indicated by the amount of product generated under given reaction conditions. For example, in efficient real-time PCR reactions, the PCR product should double at every cycle. As is known in the art, the efficiency of different kinds of amplification reactions can be calculated using different methods. For example, the exponential amplification of PCR is generally determined using the equation $$X_n = X_o * (1+E_x)^n, \quad (I)$$

where $X_n$ is the number of target molecules at cycle n, $X_o$ is the initial number of target molecules, and $E_x$ is the efficiency of the target amplification and n is the number of cycles.

Improvements in efficiency and specificity due to certain aspects of the present invention can be identified and quantified using assays known in the art and described in further detail below.

In some embodiments, dye-based qPCR detection methods are used to monitor amplification reactions utilizing components of the invention. Such detection methods generally rely on monitoring the increase in fluorescence signal due to the binding of DNA-binding dye to the amplified DNA. For example, SYBR Green I, a commonly used fluorescent DNA binding dye, binds all double-stranded DNA and detection is monitored by measuring the increase in fluorescence throughout the cycle. SYBR Green I has an excitation and emission maxima of 494 nm and 521 nm, respectively.

In other embodiments, probe-based qPCR detection methods are used to monitor amplification reactions utilizing components of the invention. Such detection methods generally rely on the sequence-specific detection of a desired PCR product. Unlike dye-based qPCR methods that detect all double-stranded DNA, probe-based qPCR utilizes a fluorescent-labeled target-specific probe, which detects specific sequences in the amplified DNA.

Ct Determination

In qPCR applications utilizing dual-labeled fluorogenic probes (such as TaqMan® probes from Applied BioSystems), the amount of cleavage product generated by 5'-3' exonuclease activity during the reaction is determined based on cycle threshold (Ct) value, which represents the number of cycles required to generate a detectable amount of DNA. In qPCR applications utilizing dual-labeled fluorogenic probes (such as TaqMan® probes from Applied BioSystems), the amount of cleavage product generated is monitored by fluorescence of a dye which is released from the fluorogenic probe through the polymerase's 5' exonuclease activity. The number of cycles required to generate a detectable amount of DNA, as monitored by dye fluorescence, is referred to as the cycle threshold (Ct). As the amount of formed amplicon increases, the signal intensity increases to a measurable level and reaches a plateau in later cycles when the reaction enters into a non-logarithmic phase. By plotting signal intensity versus the cycle number during the logarithmic phase of the reaction, the specific cycle at which a measurable signal is obtained can be deduced and used to calculate the quantity of the target before the start of the PCR. Exemplary methods of determining Ct are described in, e.g., Heid et al. Genome Methods 6:986-94, 1996. The Ct value represents the number of cycles required to generate a detectable amount of DNA (a "detectable" amount of DNA is typically 2×, 5×, 10×, 100× or more above background). An efficient polymerase may be able to produce a detectable amount of DNA in a smaller number of cycles by more closely approaching the theoretical maximum amplification efficiency of PCR. Accordingly, a lower Ct value for a given amount of input DNA template reflects a greater amplification efficiency for the enzyme.

Assays to Evaluate Processivity and Efficiency

Polymerase processivity can be measured by a variety of methods known to those of ordinary skill in the art. Polymerase processivity is generally defined as the number of nucleotides incorporated during a single binding event of a modifying enzyme to a primed template. For example, a 5' FAM-labeled primer is annealed to circular or linearized DNA to form a primed template. In measuring processivity, the primed template usually is present in significant molar excess to the polymerase so that the chance of any primed template being extended more than once by the polymerase is minimized. The primed template is therefore mixed with the polymerase at a ratio such as approximately 4000:1 (primed DNA:DNA polymerase) in the presence of buffer and dNTPs. $MgCl_2$ is added to initiate DNA synthesis. Samples are quenched at various times after initiation, and analyzed on a sequencing gel. At a polymerase concentration where the median product length does not change with time or polymerase concentration, the length corresponds to the processivity of the enzyme. The processivity of a polymerase of the invention is then compared to the processivity of a wild type enzyme.

Improvement in processivity can be reflected in the decrease in salt sensitivity of the polymerase. In some embodiments, a polymerase of the present invention tolerates higher salt concentration as its processivity is improved due to the presence of the dsDNA binding domain. For example, a PCR analysis can be performed to determine the amount of product obtained in a reaction using a polymerase of the present invention compared to a wild type polymerase in reaction mixtures with varied salt concentration. While both polymerases may produce similar amount of product at 50 mM KCl, the polymerase of the present invention is expected to outperform the wild type polymerase at higher KCl concentrations, e.g. 80 mM, 100 mM, etc.

Efficiency can be demonstrated by measuring the ability of an enzyme to produce product. Increased efficiency can be demonstrated by measuring the increased ability of an enzyme to produce product. Such an analysis measures the stability of the double-stranded nucleic acid duplex indirectly by determining the amount of product obtained in a reaction. For example, a PCR assay can be used to measure the amount of PCR product obtained with a short, e.g., 12, or 18-20 nucleotide in length, primer annealed at an elevated temperature, e.g., 50° C. In this analysis, enhanced efficiency is shown by the ability of a modified or improved polymerase to produce more product in a PCR reaction using the short primer annealed at 50° C. than a wild-type polymerase under the same conditions.

Long PCR may be used as another method of demonstrating enhanced processivity and efficiency. For example, an enzyme with enhanced processivity and efficiency typically allows the amplification of a long amplicon (>5 kb) in a shorter extension time compared to an enzyme with relatively lower processivity and efficiency.

Other methods of assessing efficiency of the polymerases of the invention can be determined by those of ordinary skill in the art using standard assays of the enzymatic activity of a given modification enzyme.

Primer/template specificity is the ability of an enzyme to discriminate between matched primer/template duplexes and mismatched primer/template duplexes. Specificity can be determined, for example, by comparing the relative yield of two reactions, one of which employs a matched primer, and one of which employs a mismatched primer. An enzyme with increased discrimination will have a higher relative yield with the matched primer than with the mismatched primer, i.e., the ratio of the yield in the reaction using the matched primer vs. the reaction using the mismatched primer is about 1 or above. This ratio can then be compared to the yield obtained in a parallel set of reactions employing a wild type polymerase. Reactions utilizing methods and compositions of the invention will in may embodiments exhibit at least a 2-fold, often 3-fold or greater increase in the ratio relative to reactions utilizing wild-type polymerases and/or standard reaction conditions.

Reaction Mixtures of the Invention

The present invention also provides reaction mixtures comprising the polymerases of the invention, the antibodies of the invention, the additives of the invention, or any combination or two or three thereof. Optionally, the antibody is complexed with the polymerase. The reaction mixtures can optionally comprise one or more dNTPs, one or more oligonucleotides, a biological sample comprising a target nucleic acid, and/or a double stranded DNA binding dye. Any one, two or more of the antibodies as described herein can be included in the reaction mixture.

Kits of the Invention

In one aspect, the present invention provides kits for conducting nucleic acid amplification reactions. In some embodiments, such kits include polymerases, and optionally dNTPs, and at least one buffer. Such kits may also include stabilizers and other additives (e.g., heparin and/or sarcosine) to increase the efficiency of the amplification reactions. Such kits may also include one or more primers as well as instructions for conducting nucleic acid amplification reactions using the components of the kits.

In a further aspect, the present invention provides kits that include components that improve the efficiency and specificity of nucleic acid amplification reactions over reactions conducted using conventional reaction conditions and reactants. Such additional components are described further herein and include without limitation hybrid polymerases, hot-start antibodies, and/or additives such as sarcosine and heparin.

In one embodiment, kits of the invention include a hybrid polymerase comprising a mutation in its polymerase domain that reduces or abolishes the polymerase's 3'-5' exonuclease activity. In a further embodiments, kits of the invention include a hybrid polymerase with an amino acid sequence substantially identical to SEQ ID NO: 2.

In some embodiments, the polymerase will be fused to a DNA binding domain. In some embodiments, the DNA binding domain will be an Sso binding domain. In some embodiments, the Sso binding domain is identical or substantially identical to SEQ ID NO:3.

In a still further embodiments, kits of the invention include a hybrid polymerase complexed with one or more specific monoclonal antibodies to achieve "hot-start" capabilities. Such monoclonal antibodies may in some exemplary embodiments comprise light-chain variable regions with nucleotide sequences of about 75%, 80%, 85%, 90%, 94%, 95%, 96%, 97%, 98%, 99% or 100% sequence identity to any one of SEQ ID NOs: 10-13. Such monoclonal antibodies may in further exemplary embodiments comprise heavy-chain variable regions with nucleotide sequences of about 75%, 80%, 85%, 90%, 94%, 95%, 96%, 97%, 98%, 99% or 100% sequence identity to any one of SEQ ID NOs: 6-9. Such monoclonal antibodies may in still further exemplary embodiments comprise heavy-chain variable regions with amino acid sequences of about 75%, 80%, 85%, 90%, 94%, 95%, 96%, 97%, 98%, 99% or 100% sequence identity to any one of SEQ ID NOs: 14-17 and/or light-chain variable regions with amino acid sequences of about 75%, 80%, 85%, 90%, 94%, 95%, 96%, 97%, 98%, 99% or 100% sequence identity to any one of SEQ ID NOs: 18-21.

In some embodiments, the antibody comprises a heavy chain variable region comprising CDR1, CDR2, and CDR3 as follows: SEQ ID NO:22, SEQ ID NO:23, and SEQ ID NO:24, respectively, and/or a light chain variable region comprising CDR1, CDR2, and CDR3 as follows: SEQ ID NO:25, SEQ ID NO:26, and SEQ ID NO:27, respectively. In some embodiments, the antibody comprises a heavy chain variable region comprising CDR1, CDR2, and CDR3 as follows: SEQ ID NO:28, SEQ ID NO:29, and SEQ ID NO:30, respectively, and/or a light chain variable region comprising CDR1, CDR2, and CDR3 as follows: SEQ ID NO:31, SEQ ID NO:32, and SEQ ID NO:33, respectively. In some embodiments, the antibody comprises a heavy chain variable region comprising CDR1, CDR2, and CDR3 as follows: SEQ ID NO:34, SEQ ID NO:35, and SEQ ID NO:36, respectively, and/or a light chain variable region comprising CDR1, CDR2, and CDR3 as follows: SEQ ID NO:37, SEQ ID NO:38, and SEQ ID NO:39, respectively.

In still further embodiments, kits of the invention include optimized buffer (Tris-HCl, pH 9.0), KCl, (NH4)2SO4, stabilizer, detergent, dNTPs, MgCl2, and DMSO.

In still further embodiments, kits of the invention include double stranded DNA binding dyes. Such double stranded DNA binding dyes can include without limitation: EvaGreen and SYBR Green, as well as any other double stranded DNA binding dyes known in the art.

In a still further embodiment, kits of the invention include additives to increase the specificity and efficiency of nucleic acid amplification reactions. Such additives include without limitation sarcosine and heparin.

It will be appreciated that kits of the invention also encompass any combination of the above-described components.

In some aspects, instructions included with kits of the invention will include typical amplification protocols that include the following steps:
- 95-98° C. for about 30 seconds to about 2 minutes
- 40 cycles (95-98° C. for about 1 to about 5 seconds, 60° C. for about 1 to about 5 seconds, detection step)
- Melting cycle at about 60° C. to about 95° C.

It will be appreciated that the above exemplary protocol can be varied using parameters well known in the art to optimize nucleic acid amplification reactions to optimize the conditions for efficiency and specificity for different target nucleic acids. For example, amplification of longer target nucleic acids may require longer incubation times and/or higher temperatures for efficient and specific amplification.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1: Comparing Primer-Dimer Formation in Reactions Utilizing Hybrid Polymerases with and without Exonuclease Activity The tendency of primer dimer formation was compared for two different polymerases. One is a hybrid polymerase enzyme (A), which has both 5'-3' polymerization activity and 3'-5' exonuclease activity for proof-reading, and the other is a mutant hybrid (B), which contains two point mutations (E141A, D143A—SEQ ID NO:2) that abolish the 3'-5' exonuclease activity without affecting the polymerase activity. Four sets of primers (a, b, c, d) were designed to present different scenarios of primer dimer formation. The characteristics of these four sets of primers were as follows:

(a) The two primers can form three G-C base pairs near but not at the 3' end of each primer.
(b) There is no tendency of primer-primer annealing based on the primer sequences.
(c) The two primers can form 3 base pairs at the 3' end.
(d) The two primers can form three A-T base pairs near but not at the 3' end of each primer.

Each of these primer pairs were pre-incubated in a reaction buffer with polymerase (A) or (B) at 45° C. for 30 minutes to promote primer dimer formation and extension, followed by a qPCR amplification protocol, so that the primer dimers formed during the pre-incubation step were further amplified. The numbers indicated in Table I are the Ct (threshold cycle) values from the qPCR amplification, and they correlate with the amount of primer dimer formed during the pre-incubation step, i.e. the smaller the Ct value the higher the amount of primer dimer formation (higher primer dimer formation is less favorable or efficient). In the experiment producing the data in Table 1, both enzymes were pre-bound to corresponding hot-start antibodies to fully inhibit the polymerase activity at low temperature.

Primer pair (a): Polymerase (A) resulted in ~14 cycle earlier Ct compared to polymerase (B). A 14 cycle difference correlates to >10000-fold difference in the amount of primer-dimer formed. It is likely that the difference arises because the 3'-5' exo nuclease activity of polymerase (A) cleaves the 3' mismatched region, and leaves a fully complimentary 3' end between the two primers, which can then be used as substrate for the polymerase activity. Conversely, polymerase (B) which lacks the 3'-5' exonuclease activity, is not able to cleave the 3' mismatched region, and the 3'-mismatched structure cannot then be efficiently utilized by the polymerase activity for extension, thus resulting in much lower level of primer-dimer formation. In this situation, polymerase (B) is the preferred enzyme.

Primer pair (b): when the primers have no tendency of annealing with each other, there is a low tendency of primer dimer formation with both polymerases.

Primer pair (c): When the primers have the tendency to form complementary sequences at the 3' end, polymerase (A) gave significantly later Ct than polymerase (B). The delay in Ct associated with polymerase (A) is likely due to the digestion of the 3' terminus of the primers by its 3'-5' exo nuclease activity, which eliminates the sequences that have the potential of forming base pairs with another primer molecule. Although, in general, it is desirable to have delayed Ct value with respect to amplification of primer dimers, in this particular case, the property of the primers are altered, both in length and in 3' sequence, which could lead to undesirable amplifications in the presence of template.

Primer pair (d): this is similar to primer pair (a) except the 3' base pairs are not as stable as those in primer pair (a). Identical Ct values are observed with both polymerases.

TABLE 1

| | (a) IL1B primers | (b) BA primers | (c) GAPD primers | (d) 18s primers |
|---|---|---|---|---|
| | 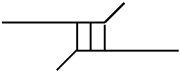 |  | 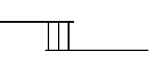 | 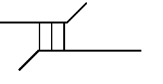 |
| | GC bp near 3' end | No bp @ or near 3' end | bp @ 3' end | AT bp near 3' |
| Enzyme (A) | 21.6 ± 0.3 | 36.5 ± 1.5 | 44.5 ± 0.9 | 33.1 ± 0.4 |
| mutant Enzyme (B) | 35.3 ± 1.3 | 34.6 ± 1.0 | 37.2 ± 3.2 | 33.4 ± 1.0 |
| dCt (A − B) | −13.7 | 1.9 | 7.3 | −0.3 |

To evaluate whether the difference observed between the two polymerases was due to the presence of the antibodies or the differences in the antibodies used, a similar assay was conducted using a hybrid and a mutant (exonuclease deficient) hybrid as described above that are not complexed with the antibodies. Four sets of primers were used (see Table 2), with set A and B containing fully complementary base pairs at the 3' end, and C containing base pairs near the 3' end followed by one base mismatch at the 3' end. With set A and B, the hybrid polymerase gave 5-8 cycle delay in Ct compared to the mutant hybrid. With set C of primers, significant earlier Ct value is obtained with hybrid polymerase compared to mutant hybrid polymerase. The overall results obtained using hybrid polymerase and mutant hybrid polymerase alone are similar to that obtained using hot start antibodies with the polymerases. Therefore, it is likely that the difference observed between the two polymerases is due to the difference in the exonuclease activity rather than the presence of antibodies.

In summary, a polymerase lacking exonuclease activity such as the mutant hybrid described above is an effective enzyme for qPCR applications to avoid primer-dimer formation/amplification in situations where primers have the tendency of forming base pairs near the 3' end and leaving mismatched bases at the 3' end, as well as to eliminate alteration of primer length/sequence in situations where primers form base pairs at the 3' end.

TABLE 2

| | A 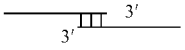 3bp match at 3' end | B 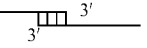 5bp match at 3' end | C 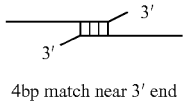 4bp match near 3' end w/ 1 mismatch |
|---|---|---|---|
| hybrid | 28.72 | 15.5 | 16.2 |
| mutant hybrid | 20.90 | 10.17 | 28.85 |
| dCt(hybrid–mutant) | 7.82 | 5.33 | −12.65 |

Figure 3:
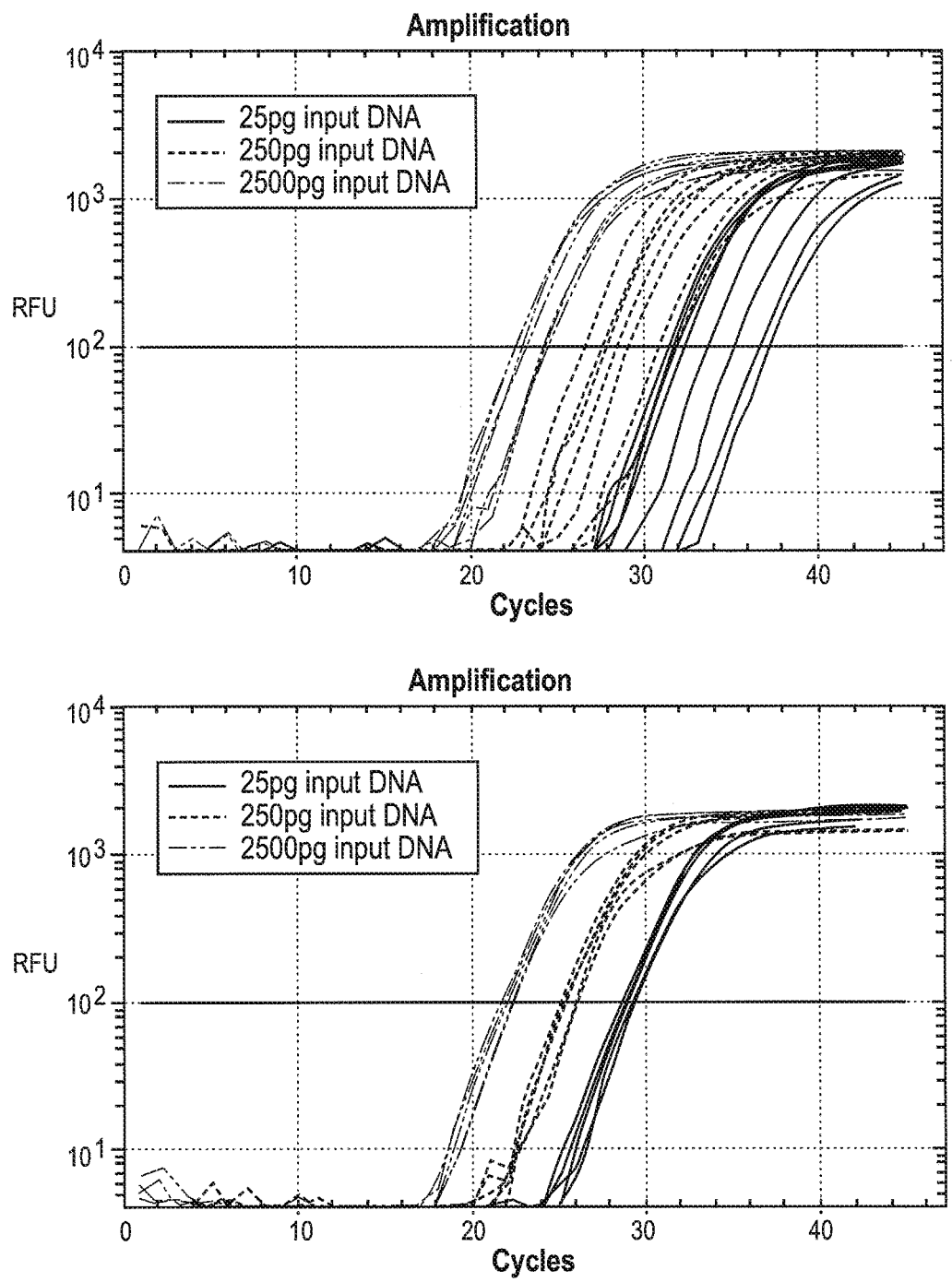
FIG. 3 shows amplification curves for different hybrid polymerases with change in annealing/extension temperature. Amplification curves for 25 pg, 250 pg, and 2500 pg input DNA are displayed.

Example 2: Comparing Amplification Efficiency of Hybrid Polymerases with and without Exonuclease Activity Additional experiments were conducted to directly compare hybrid polymerases complexed with hot-start antibodies to mutant hybrid polymerases lacking exonuclease activity, which were also complexed with the same hot-start antibodies. The same formulation composition was used with equal concentrations of either the hybrid or the mutant hybrid. The performance of the two enzymes was compared in the following two aspects: (1) ability to work with wide range of annealing/extension temperatures, and (2) ability to quantify wide range of input DNA template. Annealing and extension temperature range used is 56.6° C. to 66.6° C. The amplicon is from human beta-actin gene, and the input DNA template is 25, 250, and 2500 pg human genomic DNA per reaction. As shown in FIG. 3, the amplification curves and the Ct values obtained with the mutant hybrid (right panel) showed less deviation as the annealing/extension temperature changes from 56.6° C. to 66.6° C. In contrast, significant spread in the amplification curve and thus Ct value is observed with the hybrid polymerase (left panel) with respect to annealing/extension temperature change. In addition, hot-start hybrid gave much lower and more scattered amplification efficiency over the range of annealing/extension temperature tested, whereas hot-start mutant hybrid gave consistently higher efficiency and is not significantly affected by change of the annealing/extension temperature. (see Table 3).

TABLE 3

| Annealing/ extension temp | Efficiency of hybrid polymerase | Efficiency of mutant hybrid polymerase |
|---|---|---|
| 66.6 C. | 43.3% | 94.8% |
| 66.1 C. | 46.6% | 90.2% |
| 64.9 C. | 52.7% | 98.8% |
| 63.0 C. | 56.1% | 92.1% |
| 60.6 C. | 72.7% | 92.3% |
| 58.6 C. | 62.3% | 88.6% |
| 57.3 C. | 59.4% | 93.0% |
| 56.6 C. | 67.2% | 95.0% |

Example 3: Primer-Dimer Assays for Assessment of Hot-Start Antibodies

As described earlier, hot start DNA polymerases are used in PCR and especially real-time PCR to minimize or eliminate non-specific amplifications, as the latter is often performed in the presence of low quantities of input DNA template and is more prone to nonspecific amplifications. A primer dimer assay was developed to allow quantitative assessment of whether the hybrid polymerase or mutant polymerase described above, complexed with the appropriate antibodies, are suitable for real-time PCR applications. In this assay, a pair of primers was designed to form 3 to 5 complementary base pairs at the 3' end with each other. The assay consists of two steps: (1) the primer pair was incubated in a qPCR mix with all components required for DNA replication at 37-45° C. for 30 minutes; (2) the reaction in the first step will continue using standard qPCR cycling and detection protocol and allowed to be amplified. If the DNA polymerase was active at 37-45° C., then the primers would be extended off each other during the first step to generate templates for amplification during the second step. If the DNA polymerase was not active or has a significantly lower activity in this temperature range, then only low level of primer extension would occur during the first step, and the amplification during the second step will result in delayed Ct. Therefore, by comparing the Ct values obtained with the DNA polymerase alone versus that with the DNA polymerase complexed with the antibodies, it was possible to assess the benefit of hot start antibodies in preventing/minimizing primer dimer formation. Table 4 summarizes the results obtained using three primer sets that differ in tendency of forming base pairs at or near the 3' end. Overall, the addition of hot start antibodies resulted in 5-11 cycles of Ct delay in primer dimer amplification compared to the reactions without the addition of the antibodies. The extent of the benefit of using hot start antibodies was similar between the two polymerases.

TABLE 4

|  | a<br>3 bp match<br>at 3' end | b<br>5 bp match<br>at 3' end | c<br>4 bp match near 3'<br>end<br>w/1 mismatch at 3'<br>end |
|---|---|---|---|
| hybrid polymerase | 28.72 | 15.5 | 16.2 |
| hybrid polymerase complexed with antibodies | 35.05 | 26.43 | 22.46 |
| dCt(hybrid − (hybrid + antibodies)) | −6.33 | −10.93 | −6.26 |
| mutant hybrid polymerase | 20.90 | 10.17 | 28.85 |
| mutant hybrid polymerase complexed with antibodies | 26.03 | 16.17 | 37.82 |
| dCt(mutant hybrid − (mutant hybrid + antibodies)) | −5.13 | −6.00 | −8.97 |

Example 4: Determining Effective Concentration of Sarcosine

To determine the effective concentration range of sarcosine, different concentrations of sarcosine (from 20 mM to 540 mM) was added to a qPCR mix comprising a mutant hybrid polymerase lacking 3'-5' exonuclease activity, as described above. The effect of sarcosine on qPCR reaction efficiency was evident with sarcosine concentrations as low as 20 mM. Concentration greater than 40 mM gave optimal and similar performance (Table 6). This is in contrast to published results which showed optimal osmolyte effects at concentrations above 1M, and suggests that the mechanism of action of sarcosine in the present invention differs from published observations of the effects of osmolytes. Similar results were observed with a Sso7-Taq fusion polymerase.

TABLE 6

| | CBP amplicon (50 ng-50 pg gDNA) | |
|---|---|---|
| | Slope/R2 | Amplification efficiency |
| 0 mM | −4.466/0.980 | 67.5% |
| 20 mM | −3.688/0.997 | 86.7% |
| 40 mM | −3.352/0.997 | 98.78% |
| 60 mM | −3.370/0.991 | 98.0% |
| 80 mM | −3.386/0.987 | 97.4% |
| 100 mM | −3.329/0.998 | 104% |
| 100 mM | −3.228/0.998 | 104% |
| 200 mM | −3.341/0.991 | 99.2% |
| 300 mM | −3.177/0.995 | 106% |
| 400 mM | −3.227/0.998 | 104% |
| 540 mM | −3.150/0.995 | 108% |

Example 5: Effect of Heparin

Heparin is a negatively charged polymer that mimics the electrostatic property of dsDNA, and is commonly used for either purifying DNA binding proteins or as a nonspecific competitor for DNA binding proteins. The addition of heparin may prevent the excess DNA polymerase from binding to the double-stranded template until a single-stranded primed-template becomes available.

Figure 2:
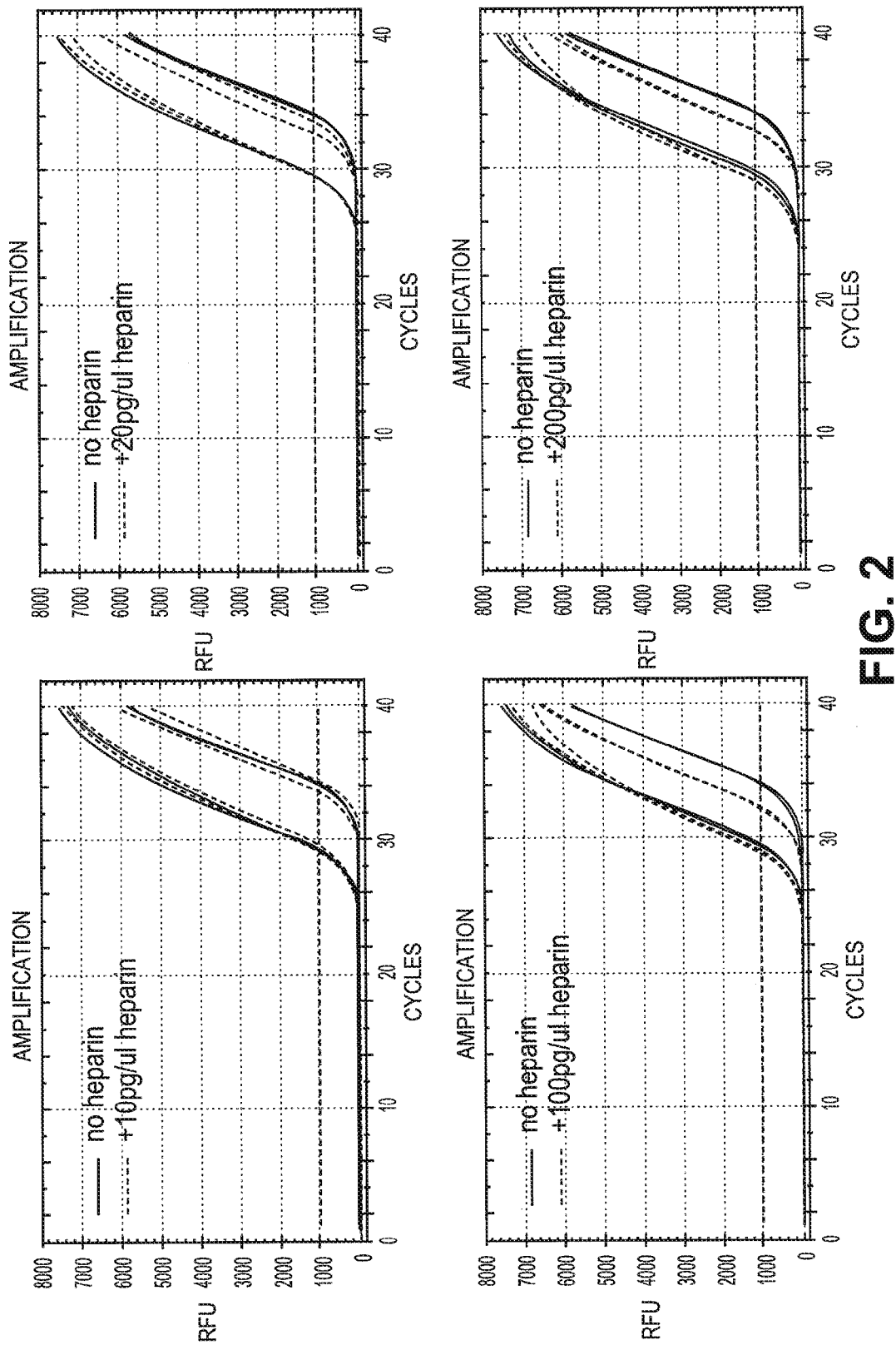
FIG. 2 shows amplification curves for reactions containing different concentrations of heparin to those with no heparin added.

A CBP amplicon was amplified in qPCR reactions from two different input amounts (5 ng and 0.5 ng) of human genomic DNA template with qPCR formulation comprising a hybrid polymerase, in which 0, 10, 20, 100, 200 pg/μl of heparin was added (FIG. 2, Table 7). If the amplification efficiency is 100%, the expected Ct difference corresponding to 10-fold difference in input template concentration is 3.33. When no heparin is added, the ΔCt between the 5 ng and 0.5 ng reactions was 4.5, which corresponds to 67% amplification efficiency. When 100 ng of heparin was added, the ΔCt between the 5 ng and 0.5 ng reactions was 3.4 corresponding to 97% amplification efficiency, which was a significant improvement in comparison to no-heparin reactions.

TABLE 7

| | no<br>Heparin | 10 pg/ul<br>Heparin | 20 pg/ul<br>Heparin | 100 pg/ul<br>Heparin | 200 pg/ul<br>Heparin |
|---|---|---|---|---|---|
| 5 ng gDNA | 25.8 | 25.8 | 25.8 | 25.3 | 25.2 |
| 0.5 ng gDNA | 30.3 | 30.3 | 29.4 | 28.7 | 28.8 |
| ΔCt (0.5 ng−5 ng) | 4.50 | 4.50 | 3.60 | 3.40 | 3.60 |
| Efficiency | 67% | 67% | 90% | 97% | 90% |

SEQUENCE LISTING (A) SEQ ID NO: 1
ATGATCCTGGATGCTGACTACATCACTGAAGAAGGCAAACCGGTTATCCGTCTGTTC
AAAAAAGAGAACGGCGAATTTAAGATTGAGCATGATCGCACCTTTCGTCCATACATT
TACGCTCTGCTGAAAGATGATTCTAAGATTGAGGAAGTTAAAAAAATCACTGCTGA
GCGCCATGGCAAGATTGTTCGTATCGTTGATGCGGAAAAGGTAGAAAAGAAATTTC
TGGGCAGACCAATCACCGTGTGGAGACTGTATTTCGAACATCCACAAGATGTTCCGA
CTATTCGCGAGAAAATTCGCGAACATTCTGCAGTTGTTGACATCTTCGAATACGATA
TTCCATTTGCAAAGCGTTACCTCATCGACAAAGGCCTGATACCAATGGAGGGCGATG
AAGAACTCAAGCTCCTGGCGTTCGCTATAGCAACCCTCTATCACGAAGGCGAAGAG
TTTGGTAAAGGCCCAATTATAATGATCAGCTATGCAGATGAAGAAGAAGCAAAGGT
GATTACTTGGAAAAAAATAGATCTCCCATACGTTGAGGTTGTATCTTCCGAGCGCGA
GATGATTAAGCGCTTTCTCAAAATTATCCGCGAGAAGGATCCGGACATTATCATTAC
TTATAACGGCGACTCTTTTGACCTCCCATATCGGCGAAACGCGCAGAAAAACTCGG
TATTAAACTGACTATCGGCCGTGATGGTTCCGAGCCGAAGATGCAGCGTATCGGCGA
TATGACCGCTGTAGAAGTTAAGGGTCGTATCCATTTCGACCTGTATCATGTAATTCG
TCGTACTATTAACCTCCCGACTTACACTCTCGAGGCTGTATATGAAGCAATTTTTGGT
AAGCCGAAGGAGAAGGTATACGCCGATGAGATTGCAAAGGCGTGGGAAACCGGTG
AGGGCCTCGAGCGTGTTGCAAAATACTCCATGGAAGATGCAAAGGCGACTTATGAA
CTCGGCAAAGAATTCTTCCCAATGGAAGCTCAGCTCTCTCGCCTGGTTGGCCAACCA
CTGTGGGATGTTTCTCGTTCTTCCACCGGTAACCTCGTAGAGTGGTTTCTCCTGCGCA

SEQUENCE LISTING

```
AAGCGTACGAACGCAACGAACTGGCTCCGAACAAGCCAGATGAACGTGAGTATGAA
CGCCGTCTCCGCGAGTCTTACGCTGGTGGCTTTGTTAAAGAGCCAGAAAAGGGCCTC
TGGGAAAACATCGTGTCCCTCGATTTTCGCGCTCTGTATCCGTCTATTATCATTACCC
ACAACGTGTCTCCGGATACTCTCAACCGCGAGGGCTGCAGAAACTATGATGTTGCTC
CGGAAGTAGGCCACAAGTTCTGCAAGGACTTCCCGGGCTTTATTCCGTCTCTCCTGA
AACGTCTGCTCGATAACGCCAAAAGATTAAGACTAAATGAAGGCGTCCCAGGAT
CCGATTGAAAAAATAATGCTCGACTATCGCCAAAGAGCGATTAAAATCCTCGCAAA
CTCTTATTACGGCTATTATGGCTATGCAAAGCACGCTGGTACTGTAAGGAGTGTGC
TGAGTCCGTTACTGCTTGGGGTCGCGAATACATCGAGTTCGTGTGGAAGGAGCTCGA
AGAAAAGTTTGGCTTTAAAGTTCTCTACATTGACACTGATGGTCTCTATGCGACTATT
CCGGGTGGTAAGTCTGAGGAAATTAAGAAAAAGGCTCTAGAATTTGTGGATTACAT
TAACGCGAAGCTCCCGGGTCTCCTGGAGCTCGAATATGAAGGCTTTTATAAACGCGG
CTTCTTCGTTACCAAGAAGAAATATGCGCTGATTGATGAAGAAGGCAAAATTATTAC
TCGTGGTCTCGAGATTGTGCGCCGTGATTGGAGCGAAATTGCGAAAGAAACTCAAG
CTAGAGTTCTCGAGGCTATTCTCAAACACGGCAACGTTGAAGAAGCTGTGAGAATTG
TAAAAGAAGTAACCAAAAGCTCTCTAAATATGAAATTCCGCCAGAGAAGCTCGCG
ATTTATGAGCAGATTACTCGCCCGCTGCATGAGTATAAGGCGATTGGTCCGCACGTG
GCTGTTGCAAAGAGACTGGCTGCTAAAGGCGTGAAAATTAAACCGGGTATGGTAAT
TGGCTACATTGTACTCCGCGGCGATGGTCCGATTAGCAACCGTGCAATTCTAGCTGA
GGAATACGATCCAGAAAGCACAAGTATGACGCAGAATATTACATTGAGAACCAGG
TGCTCCCGGCGGTACTCCGTATTCTGGAGGGTTTTGGCTACCGTAAGGAAGACCTCC
GCTGGCAAAAGACTAAACAGACTGGCCTCACTTCTTGGCTCAACATTAAAAAATCCG
GTACCGGCGGTGGCGGTGCAACCGTAAAGTTCAAGTACAAAGGCGAAGAAAAGA
GGTAGACATCTCCAAGATCAAGAAAGTATGGCGTGTGGGCAAGATGATCTCCTTCA
CCTACGACGAGGGCGGTGGCAAGACCGGCCGTGGTGCGGTAAGCGAAAAGGACGC
GCCGAAGGAGCTGCTGCAGATGCTGGAGAAGCAGAAAAAGTGA

(B) SEQ ID NO: 2
MILDADYITEEGKPVIRLFKKENGEFKIEHDRTFRPYIYALLKDDSKIEEVKKITAERHGKI
VRIVDAEKVEKKFLGRPITVWRLYFEHPQDVPTIREKIREHSAVVDIFEYDIPFAKRYLID
KGLIPMEGDEELKLLAFAIATLYHEGEEFGKGPIIMISYADEEEAKVITWKKIDLPYVEVV
SSEREMIKRFLKIIREKDPDIIITYNGDSFDLPYLAKRAEKLGIKLTIGRDGSEPKMQRIGD
MTAVEVKGRIHFDLYHVIRRTINLPTYTLEAVYEAIFGKPKEKVYADEIAKAWETGEGL
ERVAKYSMEDAKATYELGKEFFPMEAQLSRLVGQPLWDVSRSSTGNLVEWFLLRKAY
ERNELAPNKPDEREYERRLRESYAGGFVKEPEKGLWENIVSLDFRALYPSIIITHNVSPDT
LNREGCRNYDVAPEVGHKFCKDFPGFIPSLLKRLLDERQKIKTKMKASQDPIEKIMLDY
RQRAIKILANSYYGYYGYAKARWYCKECAESVTAWGREYIEFVWKELEEKFGFKVLYI
DTDGLYATIPGGKSEEIKKKALEFVDYINAKLPGLLELEYEGFYKRGFFVTKKKYALIDE
EGKIITRGLEIVRRDWSEIAKETQARVLEAILKHGNVEEAVRIVKEVTQKLSKYEIPPEKL
AIYEQITRPLHEYKAIGPHVAVAKRLAAKGVKIKPGMVIGYIVLRGDGPISNRAILAEEY
DPRKHKYDAEYYIENQVLPAVLRILEGFGYRKEDLRWQKTKQTGLTSWLNIKKSGTGG
GGATVKFKYKGEEKEVDISKIKKVWRVGKMISFTYDEGGGKTGRGAVSEKDAPKELLQ
MLEKQKK*

(C) SEQ ID NO: 3
ATVKFKYKGEEKEVDISKIKKVWRVGKMISFTYDEGGGKTGRGAVSEKDAPKELLQMLEKQKK (D) SEQ ID NO: 4
GCAACCGTAAAGTTCAAGTACAAAGGCGAAGAAAAGAGGTAGACAT
CTCCAAGATCAAGAAAGTATGGCGTGTGGGCAAGATGATCTCCTTCACCTACGACG
AGGGCGGTGGCAAGACCGGCCGTGGTGCGGTAAGCGAAAAGGACGCGCCGAAGGA
GCTGCTGCAGATGCTGGAGAAGCAGAAAAAG (E) SEQ ID NO: 5
GTGGGG (A) Heavy-chain variable region-nucleotide sequence
>M13-vh (SEQ ID NO: 6)
GAAGTACAGCTGGAGCAGTCAGGGGCTGAGCTGGTGAGGCCTGGGTCCTCAGTGAAGATTTCCT
GCAAGGCTTCTGGCTATGTTTTCAGTACCTACTGGATGAACTGGGTGAAGCAGAGGCCTGGACA
GGGTCTTGAGTGGATTGGACAGATTTATCCTGGAGATGGTGGTGTTAACTACAATGGAGAGTTC
AAGGCTAGGGCCACACTGACTGCAGACAGATCCTCCAGCACAGCCTACATGCAGCTCAGGAGCC
TAACATCTGAGGACTCTGCGGTCTATTTCTGTGCAAGTTCTTCTTACTACGTGGTAGTTCCGT
CTCCTGGCTTGCTTACTGGGGCCAAGGGACTCTGGTCTCTGTCTCTGCAGCCAAAACGACACCC
CCATCTGTCTATA >M15-vh (SEQ ID NO: 7)
GAAGTAAAGCTGGAGGAGTCAGGGGCTGAGTTGGCAAGACCTGGGGCTTCAGTGAAGTTGTCCT
GCAAGGCTTCTGGCTACACCTTTACTAGCTACTGGATGCAGTGGGTAAAACAGAGGCCTGGACA
GGGTCTGGAATGGATTGGGGCTATTTATCCTGGAGATGGTGAGACTTGGCACACTCAGAAGTTC
AAGGGCAAGGCCACATTGACTGCAGATAAATCCTCCAGCACAGCCTACATGCAACTCAGCAGCT
TGGAATCTGAGGACTCTGCGGTCTATTACTGTGCAAGAGAAAGGGATAGGTTCGACGGGTCCTG
GTTTGCTTACTGGGGCCAAGGGACTCTGGTCACTGTCTCTGCAGCCAAAACGACACCCCCATCT
GTCTATA
```

SEQUENCE LISTING

```
>M22-vh (SEQ ID NO: 8)
GAGGTAAAGCTGCAGGAGTCTGGGGCTGAGCTGGTGAGGCCTGGGGCTTCAGTGAAGCTGTCCT
GCAAGGCTTCTGGCTACACGTTCACCACCTACTGGATGAACTGGGTTAAGCAGAGGCCTGAGCA
AGGCCTTGAGTGGATTGGAAGGATTGATCCTTACGATAGTGACACTCACTACAATCAAAAGTTC
AGTGACAAGGCCATATTGACTGTAGACAAATCCTCCAGCACAGCCTACATGCAACTCAACAGCC
TGACATCTGAGGACTCTGCGGTCTATTACTGTTCAAGGGGGGACTATGTCCCCATCTATGCTAT
GGACTACTGGGGTCAAGGAACCTCAGTCACCGTCTCCTCAGCCAAAACGACACCCCCATCTGTC
TATA

>M28-vh (SEQ ID NO: 9)
GAGGTGAAGCTGGAGGAGTCAGGGGCTGAGCTGGTGAGGCCTGGGGCTTCAGTGAAGCTGTCCT
GCAAGGCTTCTGGCTACACGTTCACCACCTACTGGATGAACTGGGTTAAGCAGAGGCCTGAGCA
AGGCCTTGAGTGGATTGGAAGGATTGATCCTTACGATAGTGACACTCACTACAATCAAAAGTTC
AGTGACAAGGCCATATTGACTGTAGACAAATCCTCCAGCACAGCCTACATGCAACTCAACAGCC
TGACATCTGAGGACTCTGCGGTCTATTACTGTTCAAGGGGGGACTATGTCCCCATCTATGCTAT
GGACTACTGGGGTCAAGGAACCTCAGTCACCGTCTCCTCAGCCAAAACGACACCCCCATCTGTC
TATA (B) Light-chain variable region-nucleotide sequence
>M13-vl (SEQ ID NO: 10)
GACATTGTGATGACCCAGACTCCACTCTCCCTGCCTGTCAGTCTTGGAGATCAAGCCTCCATCT
CTTGCAGTCTAGTCAGAGCATTGTACATAGTAATGGAAACACCTATTTAGAATGGTACCTGCA
GAAACCAGGCCAGTCTCCAAAGCTCCTGATCTACAAAGTTTCCAACCGATTTTCTGGGGTCCCA
GACAGGTTCAGTGGCAGTGGATCAGGGACAGATTTCACACTCAAGATCAGCAGAGTGGAGGCTG
AGGATCTGGGACTTTATTACTGCTTTCAAGGTTCACATGTTCCGTGGACGTTCGGTGGAGGCAC
CAAGCTGGAAATCAAACGGGCTGATGCTGCACCAACTGTATCCA >M15-vl (SEQ ID NO: 11)
GACATTGTGATGACACAGACTCCAGCTTCTTTGGCTGTGTCTCTAGGGCAGAGGGCCACCATCT
CCTGCAAGGCCAGCCAAAGTGTTGATTATGATGGTGATAGTTATATGAACTGGTACCAACAGAA
ACCAGGACAGCCACCCAAACTCCTCATCTATGCTGCATCCAATCTAGAATCTGGGATCCCAGCC
AGGTTTAGTGGCAGTGGGTCTGGGACAGACTTCATCCTCAACATCCATCCTGTGGAGGAGGAGG
ATGCTGCAACCTATCACTGTCAGCAAAGTAATGAGGATCCGTGGACGTTCGGTGGAGGCACCAA
GCTGGAAATCAAACGGGCTGATGCTGCACCAACTGTATCC >M22-vl (SEQ ID NO: 12)
GATATTGTGATGACCCAGACTCCACTCTCCCTGCCTGTCAGTCTTGGAGATCAAGCCTCCATCT
CTTGCAGATCTAGTCAGAGCCTTGTACACAGTAATGGAAACACCTATTTACATTGGTACCTGCA
GAGGCCAGGCCAGTCTCCAAAGCTCCTGATCTACAAAGTTTCCAACCGATTTTCTGGGGTCCCA
GACAGGTTCAATGGCAGTGGATCAGGGACAGATTTCACACTCAAGATCAGCAGAGTGGAGGCTG
AGGATCTGGGAATTTATTTCTGCTCTCAAAGTACACATATTCCTCGGACGTTCGGTGGAGGCAC
CAAGCTGGAAATCAGACGGGCTGATGCTGCACCAACTGTATCC >M28-vl (SEQ ID NO: 13)
GATATTGTGATCACACAGTCTCCACTCTCCCTGCCTGTCAGTCTTGGAGATCAAGCCTCCATCT
CTTGCAGATCTAGTCAGAGCCTTGTACACAGTAATGGAAACACCTATTTACATTGGTACCTGCA
GAGGCCAGGCCAGTCTCCAAAGCTCCTGATCTACAAAGTTTCCAACCGATTTTCTGGGGTCCCA
GACAGGTTCAATGGCAGTGGATCAGGGACAGATTTCACACTCAAGATCAGCAGAGTGGAGGCTG
AGGATCTGGGAATTTATTTCTGCTCTCAAAGTACACATATTCCTCGGACGTTCGGTGGAGGCAC
CAAGCTGGAAATCAGACGGGCTGATGCTGCACCAACTGTATCCA (C) Heavy-chain variable region-putative amino acid sequence
>M13-vh (SEQ ID NO: 14)
EVQLEQSGAELVRPGSSVKISCKASGYVFSTYWMNWVKQRPGQGLEWIGQIYPGDGGVNYNGEF
KARATLTADRSSSTAYMQLRSLTSEDSAVYFCASSSYYGGSSVSWLAYWGQGTLVSVSAAKTTPPSVY >M15-vh (SEQ ID NO: 15)
EVKLEESGAELARPGASVKLSCKASGYTFTSYWMQWVKQRPGQGLEWIGAIYPGDGETWHTQKF
KGKATLTADKSSSTAYMQLSSLESEDSAVYYCARERDRFDGSWFAYWGQGTLVTVSAAKTTPPSVY >M22-vh (SEQ ID NO: 16)
EVKLQESGAELVRPGASVKLSCKASGYTFTTYWMNWVKQRPEQGLEWIGRIDPYDSDTHYNQKF
SDKAILTVDKSSSTAYMQLNSLTSEDSAVYYCSRGDYVPIYAMDYWGQGTSVTVSSAKTTPPSVY >M28-vh (SEQ ID NO: 17)
EVKLEESGAELVRPGASVKLSCKASGYTFTTYWMNWVKQRPEQGLEWIGRIDPYDSDTHYNQKF
SDKAILTVDKSSSTAYMQLNSLTSEDSAVYYCSRGDYVPIYAMDYWGQGTSVTVSSAKTTPPSVY (D) Light-chain variable region-putative amino acid sequence
>M13-vl (SEQ ID NO: 18)
DIVMTQTPLSLPVSLGDQASISCKSSQSIVHSNGNTYLEWYLQKPGQSPKLLIYKVSNRFSGVP
DRFSGSGSGTDFTLKISRVEAEDLGLYYCFQGSHVPWTFGGGTKLEIKRADAAPTVS >M15-vl (SEQ ID NO: 19)
DIVMTQTPASLAVSLGQRATISCKASQSVDYDGDSYMNWYQQKPGQPPKLLIYAASNLESGIPA
RFSGSGSGTDFILNIHPVEEEDAATYHCQQSNEDPWTFGGGTKLEIKRADAAPTVS
```

SEQUENCE LISTING

```
>M22-vl (SEQ ID NO: 20)
DIVMTQTPLSLPVSLGDQASISCRSSQSLVHSNGNTYLHWYLQRPGQSPKLLIYKVSNRFSGVP
DRFNGSGSGTDFTLKISRVEAEDLGIYFCSQSTHIPRTFGGGTKLEIRRADAAPTVS

>M28-vl (SEQ ID NO: 21)
DIVITQSPLSLPVSLGDQASISCRSSQSLVHSNGNTYLHWYLQRPGQSPKLLIYKVSNRFSGVP
DRFNGSGSGTDFTLKISRVEAEDLGIYFCSQSTHIPRTFGGGTKLEIRRADAAPTVS

SEQ ID NO: 22 Vh CDR1 M13
T Y W M N

SEQ ID NO: 23 Vh CDR2 M13
Q I Y P G D G G V N Y N G E F K A

SEQ ID NO: 24 Vh CDR3 M13
S S Y Y G G S S V S W L A Y

SEQ ID NO: 25 Vl CDR1 M13
K S S Q S I V H S N G N T Y L E

SEQ ID NO: 26 Vl CDR2 M13
K V S N R F

SEQ ID NO: 27 Vl CDR3 M13
F Q G S H V P W T

SEQ ID NO: 28 Vh CDR1 M15
S Y W M Q

SEQ ID NO: 29 Vh CDR2 M15
A I Y P G D G E T W H T Q K F K G

SEQ ID NO: 30 Vh CDR3 M15
E R D R F D G S W F A Y

SEQ ID NO: 31 Vl CDR1 M15
K A S Q S V D Y D G D S Y M N

SEQ ID NO: 32 Vl CDR2 M15
A A S N L E S

SEQ ID NO: 33 Vl CDR3 M15
Q Q S N E D P W T

SEQ ID NO: 34 Vh CDR1 M22
T Y W M N

SEQ ID NO: 35 Vh CDR2 M22
R I D P Y D S D T H Y N Q K F S D

SEQ ID NO: 36 Vh CDR3 M22
G D Y V P I Y A M D Y

SEQ ID NO: 37 Vl CDR1 M22
R S S Q S L V H S N G N T Y L H

SEQ ID NO: 38 Vl CDR2 M22
K V S N R F S

SEQ ID NO: 39 Vl CDR3 M22
S Q S T H I P R

SEQ ID NO: 40 Vh CDR1 M28
T Y W M N

SEQ ID NO: 41 Vh CDR2 M28
R I D P Y D S D T H Y N Q K F S D

SEQ ID NO: 42 Vh CDR3 M28
G D Y V P I Y A M D Y

SEQ ID NO: 43 Vl CDR1 M28
R S S Q S L V H S N G N T Y L H

SEQ ID NO: 44 Vl CDR2 M28
K V S N R F S
```

SEQUENCE LISTING

SEQ ID NO: 45 V1 CDR3 M28
S Q S T H I P R

What is claimed is:

1. A method of amplifying a target nucleic acid in a sample, the method comprising,
incubating said target nucleic acid in a reaction mixture comprising:
at least one primer,
an exonuclease deficient hybrid polymerase having portions of two parental polymerases, the exonuclease deficient hybrid polymerase comprising a polymerase domain and a heterologous DNA binding domain, wherein the polymerase domain is from a B family polymerase, and
a double-stranded DNA binding dye,
wherein said incubating is under conditions that permit amplification of said target nucleic acid by said hybrid polymerase; and
using quantitative polymerase chain reaction (qPCR) detection to monitor amplification of the target nucleic acid, wherein signal from the double-stranded DNA binding dye is detected in real-time;
thereby amplifying a target nucleic acid in a sample.

2. The method of claim 1, wherein the reaction mixture comprises at least two primers that can form a primer dimer.

3. The method of claim 1, wherein the reaction is initiated with antibodies bound to the hybrid polymerase.

4. The method of claim 1, wherein the reaction mixture further comprises an additive selected from the group consisting of sarcosine and heparin, in a sufficient amount to improve efficiency of the amplification reaction by at least 10% compared to a reaction mixture lacking the additive.

5. The method of claim 1, wherein the hybrid polymerase comprises SEQ ID NO:2.

6. The method of claim 1, wherein the heterologous DNA binding domain is at least 75% identical to SEQ ID NO:3.

7. The method of claim 1, wherein the hybrid polymerase comprises a polypeptide sequence at least 90% identical to SEQ ID NO:2.

* * * * *